(12) United States Patent
Salehizadeh et al.

(10) Patent No.: US 9,872,652 B2
(45) Date of Patent: Jan. 23, 2018

(54) METHOD AND APPARATUS FOR HEART RATE MONITORING USING AN ELECTROCARDIOGRAM SENSOR

(71) Applicant: University of Connecticut, Farmington, CT (US)

(72) Inventors: Seyed M. A. Salehizadeh, Coventry, CT (US); Ki H. Chon, Mansfield Center, CT (US); Yeonsik Noh, Willington, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 15/178,218

(22) Filed: Jun. 9, 2016

(65) Prior Publication Data
US 2016/0360977 A1   Dec. 15, 2016

Related U.S. Application Data

(60) Provisional application No. 62/299,944, filed on Feb. 25, 2016, provisional application No. 62/172,862, filed on Jun. 9, 2015.

(51) Int. Cl.
*A61B 5/00*   (2006.01)
*A61B 5/0205*   (2006.01)
(Continued)

(52) U.S. Cl.
CPC ............ *A61B 5/721* (2013.01); *A61B 5/0205* (2013.01); *A61B 5/0245* (2013.01);
(Continued)

(58) Field of Classification Search
CPC ..... A61B 5/7235–5/7264; A61B 5/72–5/7214; A61B 5/024; A61B 5/02405; A61B 5/0402; A61B 5/04012
See application file for complete search history.

(56) References Cited

U.S. PATENT DOCUMENTS 4,938,228 A    7/1990  Righter et al.
5,609,158 A *  3/1997  Chan .................... A61B 5/0464
                                              600/518
(Continued)

FOREIGN PATENT DOCUMENTS

EP    1 297 784 A1    4/2003
EP    1 724 684 A1    11/2006
(Continued)

OTHER PUBLICATIONS

2015 IEEE Signal Processing Cup. Available online: / http://www.zhilinzhang.com/spcup2015/.

(Continued)

*Primary Examiner* — Scott Getzow
(74) *Attorney, Agent, or Firm* — Hamilton, Brook, Smith & Reynolds, P.C.

(57) ABSTRACT

A method and corresponding apparatus employ a time-varying spectral analysis approach for reconstructing an electrocardiogram (ECG) signal that includes motion artifacts. The motion artifacts are produced by motion of an ECG sensor relative to a sensing location. The time-varying spectral analysis based approach enables the ECG signal to be reconstructed with accuracy by suppressing the motion artifacts. Example applications for the method and corresponding apparatus include ECG-based heart rate monitoring in wearable devices for fitness tracking and health monitoring even during intense physical activities.

49 Claims, 20 Drawing Sheets
(2 of 20 Drawing Sheet(s) Filed in Color)

(51) Int. Cl.
  *A61B 5/024* (2006.01)
  *A61B 5/0245* (2006.01)
  *A61B 5/04* (2006.01)
  *A61B 5/11* (2006.01)
  *A61B 5/1455* (2006.01)
  *A61B 5/046* (2006.01)
  *A61B 5/0464* (2006.01)

(52) U.S. Cl.
  CPC ...... *A61B 5/02416* (2013.01); *A61B 5/02427* (2013.01); *A61B 5/02438* (2013.01); *A61B 5/04012* (2013.01); *A61B 5/725* (2013.01); *A61B 5/7239* (2013.01); *A61B 5/7253* (2013.01); *A61B 5/0077* (2013.01); *A61B 5/02405* (2013.01); *A61B 5/046* (2013.01); *A61B 5/0464* (2013.01); *A61B 5/1102* (2013.01); *A61B 5/14552* (2013.01); *A61B 5/6824* (2013.01); *A61B 5/7275* (2013.01); *A61B 2503/10* (2013.01); *A61B 2505/07* (2013.01); *A61B 2505/09* (2013.01); *A61B 2562/0219* (2013.01)

(56) References Cited

U.S. PATENT DOCUMENTS

| | | | |
|---|---|---|---|
| 8,388,543 | B2 | 3/2013 | Chon et al. |
| 8,417,326 | B2 | 4/2013 | Chon et al. |
| 8,998,815 | B2 | 4/2015 | Venkatraman et al. |
| 2008/0109041 | A1 | 5/2008 | De Voir |
| 2008/0167564 | A1 | 7/2008 | Hete et al. |
| 2009/0069703 | A1 | 3/2009 | Takla et al. |
| 2011/0066041 | A1* | 3/2011 | Pandia .............. A61B 5/113 600/484 |
| 2012/0123232 | A1 | 5/2012 | Najarian et al. |
| 2014/0005988 | A1* | 1/2014 | Brockway .......... H03H 17/0248 703/2 |
| 2014/0222350 | A1* | 8/2014 | Zheng .............. A61B 5/04017 702/19 |
| 2014/0275852 | A1 | 9/2014 | Hong et al. |
| 2014/0275854 | A1 | 9/2014 | Venkatraman et al. |
| 2016/0361021 | A1 | 12/2016 | Salehizadeh et al. |

FOREIGN PATENT DOCUMENTS

| | | |
|---|---|---|
| EP | 1 757 224 A2 | 2/2007 |
| EP | 2 792 297 A1 | 10/2014 |
| WO | WO 03/000125 A1 | 1/2003 |
| WO | WO 2011/026669 A1 | 3/2011 |
| WO | WO 2012/100175 A1 | 7/2012 |
| WO | WO 2012/123828 A1 | 9/2012 |
| WO | WO 2016/201130 | 12/2016 |
| WO | WO 2017/019184 A2 | 2/2017 |
| WO | WO 2017019184 A2 | 2/2017 |

OTHER PUBLICATIONS

Boreom Lee, et al., "Improved Elimination of Motion Artifacts From a Photoplethysmographic Signal Using a Kalman Smoother With Simultaneous Accelerometry," *Physiological Measurement*, 31(12):1585 (2010).
Salehizadeh, S., et al., "Photoplethysmograph Signal Reconstruction Based on a Novel Motion Artifact Detection-Reduction Approach. Part II: Motion and Noise Artifact Removal," *Ann. Biomed. Eng.*, 42:2251-2263 (2014).
Dash S., Chon, K.H. Raeder E."Automatic real time detection of atrial fibrillation", Ann Biomed Eng, Sep. 2009;37(9):1701-9.
Dash, S., et al., "Estimation of Respiratory Rate From ECG, Photoplethysmogram, and Piezoelectric Pulse Transducer Signals: A Comparative Study of Time– Frequency Methods," *Biomedical Engineering, IEEE Transactions on*, 57(5):1099-1107 (2010).
Deepak Vala, D.T.P., "A Survey on Ambulatory ECG and Identification of Motion Artifact," *International Journal of Engineering Research and Development*, 1(7):38-41 (2012).
Devlin PH, M.R., and Ketchum, J.W., "Detection Electrode Motion Noise in ECG Signals by Monitoring Electrode Impedance," *Computers in Cardiology*, p. 51-56 (1984).
Hamilton, P.S., et al., "Comparison of Methods for Adaptive Removal of Motion Artifact," *Computers in Cardiology*, 2000 (2000).
Hamilton, P.S., et al., "Effect of Adaptive Motion-Artifact Reduction on QRS Detection," *Biomed Instrum. Technol.*, 34(3):197-202 (2000).
Hashim, F.R., et al., "Wavelet Based Motion Artifact Removal for ECG Signals," In: IEEE EMBS International on Biomedical Engineering and Sciences (IECBES). Langkawi: IEEE: 2012, 339-342.
Hyvärinen, A. and Oja, E., "Independent Component Analysis: Algorithms and Applications," *Neural Networks*, 13(4-5):411-430 (2000).
Jinseok, L., et al., "Automatic Motion and Noise Artifact Detection in Holter ECG Data Using Empirical Mode Decomposition and Statistical Approaches," *Biomedical Engineering, IEEE Transactions on*, 59(6):1499-1506 (2012).
Kalman, R.E., "A New Approach to Linear Filtering and Prediction Problems," *Trans. ASME J. Basic Eng.*, 82:35-45 (1960).
Kearney, K., et al., "Quantification of Motion Artifact in ECG Electrode Design," *Engineering in Medicine and Biology Society, EMBS 2007. 29th Annual International Conference of the IEEE*, (2007).
Kim, B.S. and Yoo, S.K., "Motion Artifact Reduction in Photoplethysmography Using Independent Component Analysis," *IEEE Trans. Biomed. Eng.*,53:566-568 (2006).
Krishnan, R., B., et al., "Two-Stage Approach for Detection and Reduction of Motion Artifacts in Photoplethysmographic Data," *Biomedical Engineering, IEEE Transactions on*, 57(8):1867-1876 (2010).
Maeda, Y., et al., "Relationship Between Measurement Site and Motion Artifacts in Wearable Reflected Photoplethysmography," *J Med Syst*, 35(5):969-76 (2011).
Rahman, M.Z.U., et al., "An Efficient Noise Cancellation Technique to Remove Noise From the ECG Signal Using Normalized Signed Regressor LMS Algorithm," *Bioinformatics and Biomedicine, BIBM '09, IEEE International Conference on* (2009). 257-260.
Raya, M.A.D. and Sison, L.G., "Adaptive Noise Cancelling of Motion Artifact in Stress ECG Signals Using Accelerometer," *Engineering in Medicine and Biology, 24th Annual Conference and the Annual Fall Meeting of the Biomedical Engineering Society EMBS/BMES Conference, Proceedings of the Second Joint* (2002). 1756-1757.
Reyes, B.A., et al., "Novel Electrodes for Underwater ECG Monitoring," *IEEE Trans Biomed Eng.*, 61(6):1863-76 (2014).
Salehizadeh, S., et al., "A Novel Time-Varying Spectral Filtering Algorithm for Reconstruction of Motion Artifact Corrupted Heart Rate Signals During Intense Physical Activities Using a Wearable Photoplethysmogram Sensor," *Sensors*, 16(1):10 (2016).
Sarmiento, S., et al., "Heart Rate Variability During High-Intensity Exercise", *Journal of Systems Science and Complexity*, 26(1):104-116 (2013).
Seyedtabaii, S.S.A.L., "Kalman Filter Based Adaptive Reduction of Motion Artifact From Photoplethysmographic Signal," *World Acad. Sci. Eng. Technol.*, 37:136-137 (2008).
Temko, A., "Estimation of Heart Rate From Photoplethysmography During Physical Exercise Using Wiener Filtering and the Phase Bocoder," *37th Annual International Conference of the IEEE Engineering in Medicine and Biology Society* (2015).
Thakor, N.V. and Yi-Sheng, Z., "Applications of Adaptive Filtering to ECG Analysis: Noise Cancellation and Arrhythmia Detection," *Biomedical Engineering, IEEE Transactions on*, 38(8):785-794 (1991).
Wang, H., et al., "A High Resolution Approach to Estimating Time-Frequency Spectra and Their Amplitudes," *Annals of Biomedical Engineering*, 34(2):326-338 (2006).

(56) References Cited

OTHER PUBLICATIONS

Yao, J. and Warren, S. "A Short Study to Assess the Potential of Independent Component Analysis for Motion Artifact Separation in Wearable Pulse Oximeter Signals," *IEEE Eng. Med. Biol. Soc. Conf Proc.*, 4:3585-3588 (2005).

Yilmaz, T., et al. ,"Detecting Vital Signs With Wearable Wireless Sensors," *Sensors*, 10(12):10837 (2010).

Yoon, H. et al., "An Automated Motion Artifact Removal Algorithm in Electrocardiogram Based on Independent Component Analysis", in *The Fifth International Conference on eHealth, Telemedicine, and Social Medicine*, Nice, France. p. 15-20 (2013).

Zhang, Z., "Photoplethysmography-Based Heart Rate Monitoring in Physical Activities Via Joint Sparse Spectrum Reconstruction," *Biomedical Engineering, IEEE Transactions* PP(99):1,1 (2015).

Zhang, Z., et al., "TROIKA: A General Framework for Heart Rate Monitoring Using Wrist-Type Photoplethysmographic Signals During Intensive Physical Exercise," *IEEE Trans. on Biomedical Engineering*, 62(2):522-531 (2015).

International Search Report and Written Opinion for Int'l Application No. PCT/US2016/036743, titled: Method and Apparatus for Heart Rate Monitoring Using an Electrocardiogram Sensor, dated Aug. 30, 2016.

Zhang, F. et al., "Novel QRS Detection by CWT for ECG Sensor," Biomedical Circuits and Systems Conference, 2007, BIOCAS 2007, IEEE, Piscataway, NJ, USA, Nov. 27, 2007, pp. 211-214.

\* cited by examiner

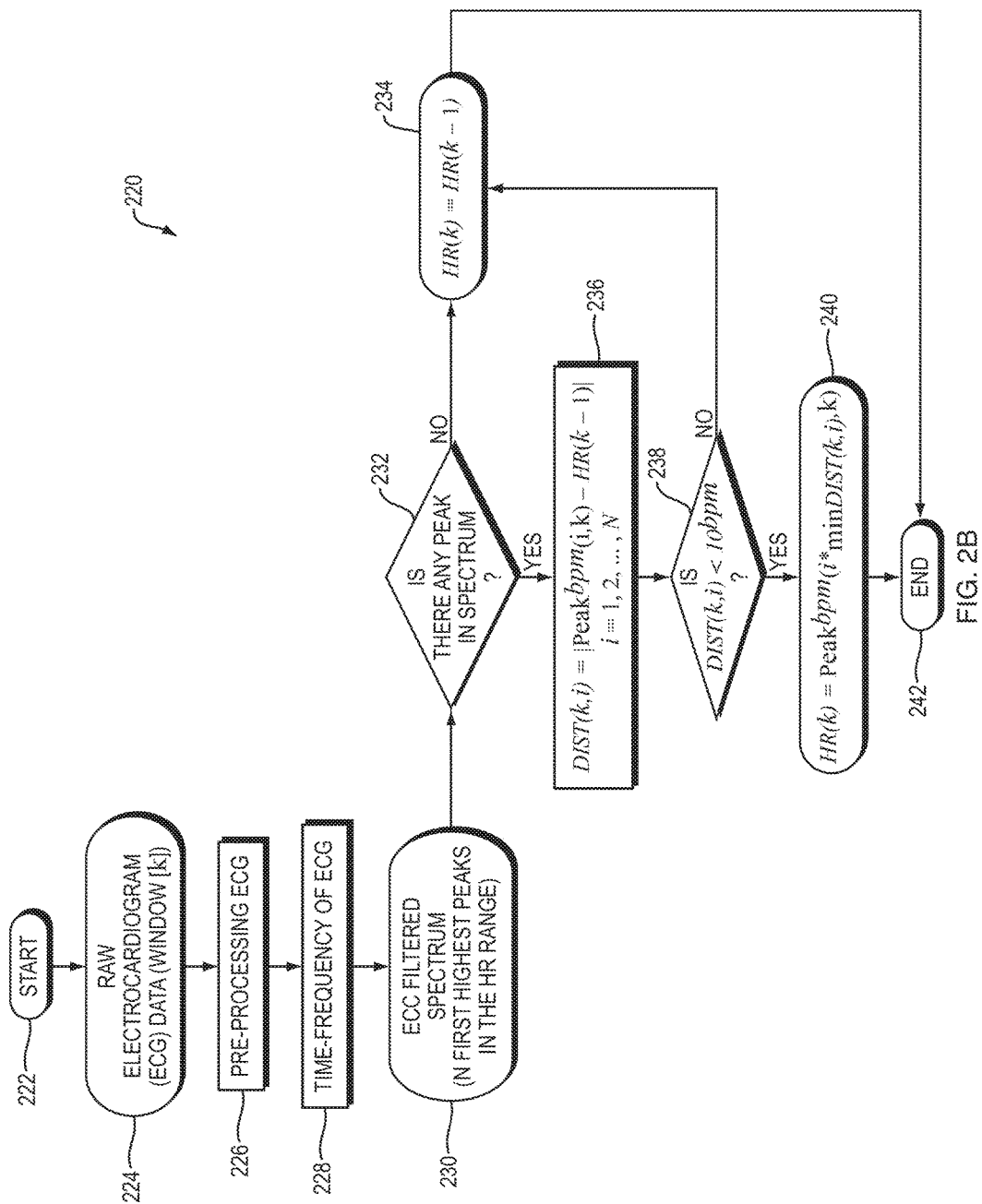

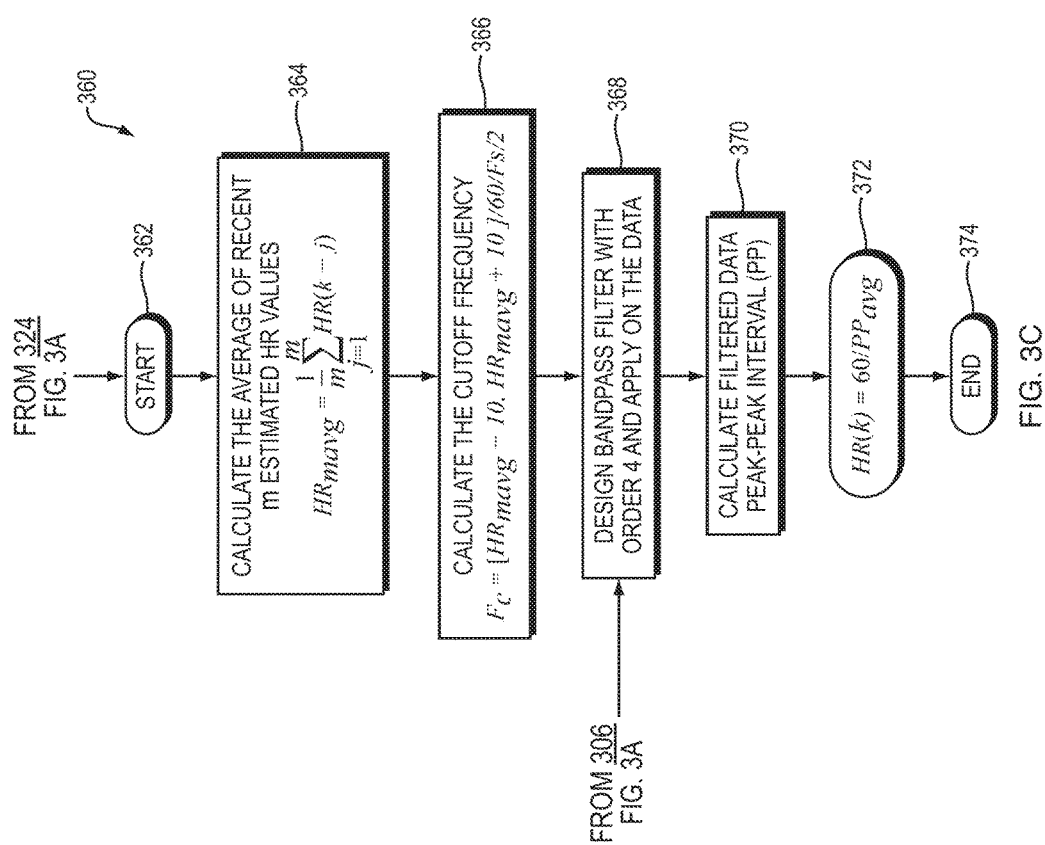

METHOD AND APPARATUS FOR HEART RATE MONITORING USING AN ELECTROCARDIOGRAM SENSOR

RELATED APPLICATIONS

This application claims the benefit of U.S. Provisional Application No. 62/172,862 filed Jun. 9, 2015 and U.S. Provisional Application No. 62/299,944 filed Feb. 25, 2016. The entire teachings of the above applications are incorporated herein by reference.

GOVERNMENT SUPPORT

This invention was made with government support under Grant No. W81WH-12-1-0541 from the US Army Medical Research and Material Command (USAMRMC). The government has certain rights in the invention.

BACKGROUND

Cardiovascular disease is the leading cause of death in the world. Considering the fact that a majority of such deaths due to cardiac arrest occur before a patient can get the needed medical care, the patient should be continuously monitored for real time detection of events that can portend cardiac arrest (Deepak Vala, D.T.P., A Survey on Ambulatory ECG and Identification of Motion Artifact. International Journal of Engineering Research and Development, 2012. 1(7): p. 38-41). The electrocardiogram (ECG) is a main measurement device for effectively diagnosing cardiovascular health, and other cardio-respiratory related diseases, and can be used as a guide for cardio-fitness therapy.

SUMMARY OF THE INVENTION

During exercise and other activities, ECG and other sensors may experience movement, such as shifting position or rotating, relative to a sensing location (e.g., wrist or chest). The movement typically results in an introduction of a motion artifact in an electrical signal produced by the sensor. The motion artifact may be interpreted by a processor as a heart-related signal if not addressed in advance of or as part of the processing in the processor. By properly addressing the motion artifact, an embodiment disclosed herein has improved accuracy in reconstructing the heart-related signal, thereby enabling processes that use the heart-related signal to have better performance.

Accordingly, a method for reconstructing a heart-related signal output by a biomedical sensor may comprise pre-processing the heart-related signal to produce a pre-processed heart-related signal. The method may further comprise reconstructing a representation of the heart-related signal to produce a reconstructed representation of the heart-related signal. The reconstructing may be based on a time-varying spectral analysis of the pre-processed heart-related signal, the heart-related signal including motion artifacts. The motion artifacts may be signal artifacts produced by movement of the biomedical sensor relative to a sensing location. The pre-processing may reduce the motion artifacts in the pre-processed heart-related signal for the reconstructing. The method may further comprise outputting the reconstructed representation of the heart-related signal.

The biomedical sensor may be an electrocardiogram (ECG) sensor.

The reconstructing may further reduce the motion artifacts reduced by the pre-processing.

The pre-processing may include down-sampling the heart-related signal to produce a down-sampled heart-related signal, the down-sampling being at a sampling rate less than an original sampling rate.

The time-varying spectral analysis may be based on a frequency resolution and the down-sampling may affect the frequency resolution of the time-varying spectral analysis.

The pre-processing may include computing a derivative of the down-sampled heart-related signal to reduce the motion artifacts.

The pre-processing may further include computing an absolute value of the derivative to further reduce the motion artifacts.

The time-varying spectral analysis may include computing a time-frequency spectrum (TFS) of the pre-processed heart-related signal.

The TFS computed may be a 3-dimensional spectra including a time-varying amplitude or power distribution with respect to time and frequency.

The TFS computed may be a time-varying power spectral density (PSD).

The method may further include limiting the TFS computed to a given frequency range. The given frequency range may be 0.5 Hz to 3 Hz.

The TFS may be computed for each shift of a windowed data segment of the pre-processed heart-related signal and the heart related signal may be reconstructed for each shift of the windowed data segment.

At each shift of the windowed data segment subsequent to an initial windowed data segment, the method may further include retaining up to a pre-determined number of frequency spectra to produce a subset of frequency spectra. The method may further include selecting a frequency component to produce a selected frequency component for the reconstructing. The selected frequency component may be selected from amongst frequency components of the subset of frequency spectra and a previous frequency component. The previous frequency component may have been selected for a previous shift of the windowed data segment to reconstruct the heart-related signal for the previous shift.

The time-varying spectral analysis may be a first time-varying spectral analysis. The reconstructing may be further based on a second time-varying spectral analysis of a motion signal, the motion signal output by a motion sensor and representative of the motion artifacts in the heart-related signal.

The method may further include employing the second time-varying spectral analysis of the motion signal to produce a movement classification of the movement, and wherein the reconstructing is further based on the classification of the movement.

The heart-related signal and the motion signal may be output, concurrently.

The biomedical sensor and the motion sensor may be co-located.

The motion sensor may be an accelerometer.

The method may further comprise employing the reconstructed representation to determine a heart rate estimate.

The method may further comprise employing the reconstructed representation to determine a heart rate variability (HRV) estimate.

The method may further comprise employing the reconstructed representation to detect or predict a heart-related ailment, the heart-related ailment including at least one of a heart rate variability (HRV) condition, atrial fibrillation condition, congestive heart failure condition, and tachycardia condition.

The pre-processing, the reconstructing, and the outputting may be performed in real-time with respect to outputting of the heart-related signal by the biomedical sensor.

The pre-processing, the reconstructing, and the outputting may be performed in non-real-time with respect to outputting of the heart-related signal by the biomedical sensor.

According to another embodiment, an apparatus for reconstructing a heart-related signal output by a biomedical sensor may comprise a pre-processing unit configured to pre-process the heart-related signal to produce a pre-processed heart-related signal. The apparatus may further comprise a reconstruction unit. The reconstruction unit may be configured to reconstruct a representation of the heart-related signal to produce a reconstructed representation of the heart-related signal. The reconstructing may be based on a time-varying spectral analysis of the pre-processed heart-related signal. The heart-related signal may include motion artifacts, the motion artifacts being signal artifacts produced by movement of the biomedical sensor relative to a sensing location. The pre-processing unit may reduce the motion artifacts in the pre-processed heart-related signal for the reconstructing. The method may further comprise an output unit configured to output the reconstructed representation of the heart-related signal.

Yet another example embodiment may include a non-transitory computer-readable medium having stored thereon a sequence of instructions which, when loaded and executed by a processor, causes the processor to complete methods disclosed herein.

It should be understood that embodiments disclosed herein can be implemented in the form of a method, apparatus, system, or computer readable medium with program codes embodied thereon.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 2A-B are flow diagrams of an example embodiment of a method for reconstructing a heart-related signal output by a biomedical sensor.

FIG. 2B is a flow diagram of another example embodiment of a method for reconstructing a heart-related signal output by a biomedical sensor.

FIGS. 3A-C are flow diagrams of example embodiments of yet another method for reconstructing a heart-related signal output by a biomedical sensor.

DETAILED DESCRIPTION OF THE INVENTION

Figure 1A:
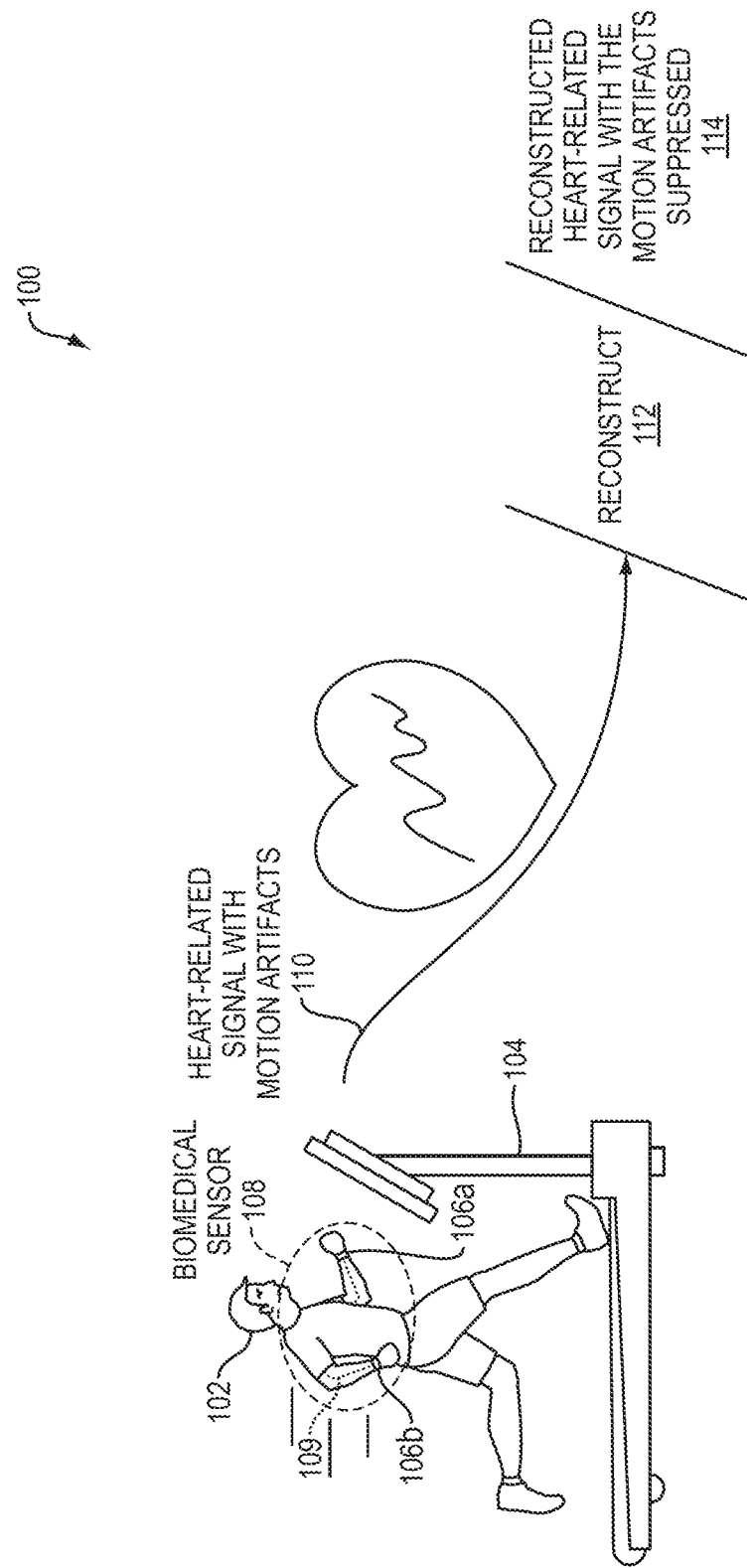
FIG. 1A is a block diagram of an example application for which embodiments disclosed herein may be applied.

A description of example embodiments of the invention follows.

Accurate estimation of heart rates from electrocardiogram (ECG) signals during intense physical activity is a very challenging problem. This is because strenuous and high intensity movements can result in severe motion artifacts in the ECG signals, making accurate heart rate (HR) estimation difficult.

For detecting infrequent and episodic cardiac arrhythmias, a Holter monitor is commonly used for continuous monitoring of ECG which can last more than several days. Additionally, to ensure that exercises are effective, during aerobic exercise, a heart-rate monitor provides a user with information such as the specific heart-rate zone, calories burned, and breathing rate. In addition, as a possible diagnostic outcome underlying many autonomic dysfunction, heart rate variability (HRV) information from wearable sensors including devices that use ECG will become more relevant as these wearable devices are personalized (Achten, J. and A. E. Jeukendrup, Heart rate monitoring: applications and limitations. Sports medicine (Auckland, N. Z.), 2003. 33(7): p. 517-538). Increased HRV has been associated with lower mortality rates and is affected by both age and gender. During graded exercise, the majority of studies show that HRV decreases progressively up to moderate intensities, after which it stabilizes (Laughlin, M. H., Cardiovascular response to exercise. Am J Physiol, 1999. 277(6 Pt 2): p. S244-59).

Wearable health monitoring systems (WHMS) enable continuous, reliable and long-term monitoring of vital signs and physiological signals during daily normal activities. Recently, a variety of WHMS have also been introduced in an attempt to reduce size, improve comfort and accuracy, and extend the duration of monitoring. Product concepts and prototypes of ECG patches have been introduced by several companies and research groups such as: Curvus, Corventis, iRhythm, Toumaz and Delta. Researchers in (F. Yazicioglu, T. T., J. Penders, I. Romero, H. Kim, P. Merken, B. Gyselinckx, H. J. Yoo, C. Van Hoof. Ultra-low-power wireless sensor nodes. in Proceedings of the 31st Annual International Conference of the IEEE EMBS. 2009. Minneapolis: IEEE; J. Penders, J.v.d.M., M. Altini, F. Yazicioglu and C.

Van Hoof. A low-power wireless ECG necklace for reliable cardiac activity monitoring on-the-move. in Proceedings of the International Conference of the IEEE Engineering in Medicine and Biology Society. 2011. IEEE) developed an ultra-low-power ECG platform and a low-power wireless ECG necklace. Samsung created a research WHMS prototype, Simband, for continuous monitoring of ECG and Electrocardiogram (ECG) signals (Aubert, A. E., B. Seps, and F. Beckers, Heart rate variability in athletes. Sports Med, 2003. 33(12): p. 889-919). Wearable and wireless devices allow delocalizing ECG monitoring from hospitals to home environments. Achieving reliable and high integrity recording however remains a challenge in ambulatory conditions due to the high level of noise introduced by motion artifacts. The effectiveness of WHMS can be significantly impaired by motion artifacts which contaminate the signal and that can lead to errors in estimation of cardiac parameters and trigger false alarms. For Holter systems, motion artifacts often lead to difficult interpretation of whether or not certain arrhythmia has truly occurred even when three or five different channels of ECG data are considered.

Reducing the motion artifacts would extend the applicability of ambulatory monitors to situations of greater activity as encountered in most daily-life situations. Skin forms a physiological barrier for diffusion of water and ions, and it is charged with a relatively high trans-dermal potential of typically −10 to −30 mV. The potential is generated by a constant ionic gradient and ionic potential of sweat glands (Kearney, K., C. Thomas, and E. McAdams. Quantification of Motion Artifact in ECG Electrode Design. in Engineering in Medicine and Biology Society, 2007. EMBS 2007. 29th Annual International Conference of the IEEE. 2007). The relatively thin (typically between 2 and 20 µm) barrier has a very high resistance but allows a capacitive coupling at conventional ECG frequencies. The temporally and spatially varying skin potential accounts for the generation of low frequency noise and artifacts (Kearney, K., C. Thomas, and E. McAdams. Quantification of Motion Artifact in ECG Electrode Design. in Engineering in Medicine and Biology Society, 2007. EMBS 2007. 29th Annual International Conference of the IEEE. 2007).

Noise and motion artifacts are also caused by several factors, such as baseline wander (BW), power-line interference (PLI), electromyography (EMG) noise and skin-electrode motion artifacts (MA) (Friesen, G. M., et al., A comparison of the noise sensitivity of nine QRS detection algorithms. Biomedical Engineering, IEEE Transactions on, 1990. 37(1): p. 85-98). In practice, motion artifacts (MAs) are difficult to remove because they do not have a predefined narrow frequency band and their spectrum often overlaps that of the ECG signal (Thakor, N. V. and Y. S. Zhu, Applications of adaptive filtering to ECG analysis: noise cancellation and arrhythmia detection. IEEE Trans Biomed Eng, 1991. 38(8): p. 785-94). Several electrical models have been proposed to characterize skin-electrode interface (Webster, N. T. a. J. The origin of skin potential and its variations. in Proc. Ann. Conf. Eng. Biol. Med 1978; Edelberg, R., Local electrical response of the skin to deformation. J Appl Physiol, 1973. 34(3): p. 334-40; Muhlsteff, J. and O. Such. Dry electrodes for monitoring of vital signs in functional textiles. in Engineering in Medicine and Biology Society, 2004. IEMBS '04. 26th Annual International Conference of the IEEE. 2004).

The corruption introduced by motion artifacts are random variables which depend on the electrode properties, electrolyte properties, skin impedance, and a movement of the patient. Deformation in the skin produces changes in the impedance of the uppermost layers of the skin that are translated into changes in potential measured at the body surface (Comert, A. and J. Hyttinen, Investigating the possible effect of electrode support structure on motion artifact in wearable bioelectric signal monitoring. Biomed Eng Online, 2015. 14: p. 44). In addition, relative motion of the electrode and skin under motion leads to a charge deformation at the electrode-skin boundary. Consequently, development of methods capable of reconstructing the corrupted signal and removing artifacts is challenging.

Numerous methods for motion artifact detection and reduction have been proposed in literature. Traditional denoising techniques are based on time averaging (Afonso, V. X., et al., Comparing stress ECG enhancement algorithms. Engineering in Medicine and Biology Magazine, IEEE, 1996. 15(3): p. 37-44) and frequency analysis such as filter banks (Afonso, V. X., et al., Comparing stress ECG enhancement algorithms. Engineering in Medicine and Biology Magazine, IEEE, 1996. 15(3): p. 37-44) or wavelet transforms (P., A. Separating cardiac and muscular ECG components using adaptive modelling in time-frequency domain. in Proc. of the WACBE World Congress on Bioengineering. 2007). In adaptive filtering, a filter is applied after adjusting its parameters to a time varying noise. This is particularly useful when the noise is non-stationary, like in the case of ambulatory motion artifacts. However, a reference signal has to be additionally recorded together with the ECG. Several adaptive filtering approaches have been proposed to obtain an adequate reference signal such as measurement of skin-electrode impedance (Devlin PH, M. R., Ketchum J W., Detection electrode motion noise in ecg signals by monitoring electrode impedance. Computers in Cardiology, 1984: p. 51-56; Hamilton, P. S., et al. Comparison of methods for adaptive removal of motion artifact. in Computers in Cardiology 2000. 2000), skin stretching measured with optical sensors (Hamilton, P. S., et al. Comparison of methods for adaptive removal of motion artifact. in Computers in Cardiology 2000. 2000; Hamilton, P. S., M. Curley, and R. Aimi, Effect of adaptive motion-artifact reduction on QRS detection. Biomed Instrum Technol, 2000. 34(3): p. 197-202) or accelerometers (Tong, D. A., K. A. Bartels, and K. S. Honeyager. Adaptive reduction of motion artifact in the electrocardiogram. in Engineering in Medicine and Biology, 2002. 24th Annual Conference and the Annual Fall Meeting of the Biomedical Engineering Society EMBS/BMES Conference, 2002. Proceedings of the Second Joint. 2002; Raya, M. A. D. and L. G. Sison. Adaptive noise cancelling of motion artifact in stress ECG signals using accelerometer. in Engineering in Medicine and Biology, 2002. 24th Annual Conference and the Annual Fall Meeting of the Biomedical Engineering Society EMBS/BMES Conference, 2002. Proceedings of the Second Joint. 2002; Thakor, N. V. and Z. Yi-Sheng, Applications of adaptive filtering to ECG analysis: noise cancellation and arrhythmia detection. Biomedical Engineering, IEEE Transactions on, 1991. 38(8): p. 785-794). Raya and Sison (Raya, M. A. D. and L. G. Sison. Adaptive noise cancelling of motion artifact in stress ECG signals using accelerometer in Engineering in Medicine and Biology, 2002. 24th Annual Conference and the Annual Fall Meeting of the Biomedical Engineering Society EMBS/BMES Conference, 2002. Proceedings of the Second Joint. 2002) used an accelerometer to reduce the motion artifacts (M A) of ECG signals.

However, the least mean square (LMS) and recursive least square (RLS) were unable to provide acceptable results. MA is difficult to detect because every movement of muscles are different for each person, thus a generalized method that takes into account various MA features may be difficult to develop. As sources of ECG and motion artifacts are uncorrelated, blind source separation (BSS) techniques could be used for separating both signals (Hyvarinen, A. and E. Oja, Independent component analysis: algorithms and applications. Neural Networks, 2000. 13(4-5): p. 411-430; Castells, F., A. Cebrian, and J. Millet, The role of independent component analysis in the signal processing of ECG recordings. Biomed Tech (Berl), 2007. 52(1): p. 18-24; Heenam Yoon, H. K., Sungjun Kwon, Kwangsuk Park, An Automated Motion Artifact Removal Algorithm in Electrocardiogram Based on Independent Component Analysis, in The Fifth International Conference on eHealth, Telemedicine, and Social Medicine. 2013: Nice, France. p. 15-20).

In order to apply BSS techniques, input signals should be linearly independent. In the case of ECG signals, a multi-lead ECG recording in which the leads are linearly independent is required. Principal Component Analysis (PCA) has been used for reducing noise in single lead ECG segmented in time intervals (Palaniappan R, K. T. Unichannel PCA for noise reduction from ECG signals. 2004). A combination of PCA and ICA was also proposed by Chawla (Chawla, M. P. S., A comparative analysis of principal component and independent component techniques for electrocardiograms. Neural Computing and Applications, 2009. 18(6): p. 539-556) for ECG de-noising. Lee et al. used empirical mode decomposition (EMD) approach to detection of Motion and noise artifact for the purpose of detection of atrial fibrillation from ECG recordings (Jinseok, L., et al., Automatic Motion and Noise Artifact Detection in Holter ECG Data Using Empirical Mode Decomposition and Statistical Approaches. Biomedical Engineering, IEEE Transactions on, 2012. 59(6): p. 1499-1506). The main issue with BSS methods is its heavy computational cost and that they are not suitable for real-time processing purposes.

Embodiments disclosed herein enable accurate reconstruction of motion-corrupted electrocardiogram (ECG) signals and HR based on a time-varying spectral analysis. A spectral filter approach for electrocardiogram motion artifacts and heart rate reconstruction (SegMA) may be referred to interchangeably herein as a SegMA method or SegMA.

According to some embodiments, the SegMA method may comprise 5 distinct stages: (1) Taking a derivative of a downsampled ECG signal, (2) obtaining a time-varying power spectral density (PSD) of an absolute value of the derivative, (3) spectral filtering, (4) HR reconstruction, and (5) Heart Rate Variability Analysis.

Embodiments disclosed herein may compute a time-frequency spectrum of an ECG signal for each time shift of a windowed data segment of the ECG signal. By analyzing time-varying spectra of the ECG, those frequency spectra belonging to the HR can be distinguished from the ECG spectrum. Embodiments disclosed herein may preserve (i.e., retain) spectra corresponding to a highest power in the time-frequency spectrum, the most dominant frequency components of the resulting spectrum in each window may represent the HR and may be extracted for each window segment.

The SegMA approach according to embodiments disclosed herein was applied to datasets recorded in Chon Lab that include 17 min recordings from 10 subjects during a challenging experimental protocol including walking, jogging, running, arm movement, wrist movement, body shaking, and weight lifting activities. ECG and tri-axial accelerometer data were recorded from wrist bands on both right and left wrists of the subjects connected with wire through a tight suit. Reference ECG signals were recorded from the subjects' chests' using a respective Holter monitor.

The reference ECG signals were recorded to compare a performance of the SegMA method. The method's accuracy was calculated by computing the mean absolute error between SegMA reconstructed HR from the wrist ECG and the reference HR from the Holter ECG. Average estimation errors using the SegMA method on these datasets is less than 2 beats/min. Moreover, it was found that dynamics of heart rate variability (HRV) measures in both time- and frequency-domains can be accurately captured using the SegMA method where the mean Pearson's correlation coefficient was found to be 0.96 between the power spectral densities of the reference and the reconstructed heart rate time series; there was no significant difference between the reference and reconstructed HRV time-domain parameters.

These results show that the SegMA method has a potential for ECG-based HR monitoring in wearable devices for fitness tracking and health monitoring during intense physical activities.

FIG. 1A is a block diagram 100 of an example application for which embodiments disclosed herein may be applied. In FIG. 1A, a subject 102 is running on a treadmill 104. The subject 102 is wearing wrist bands 106a and 106b that include respective electrodes, such as carbon black (CB) electrodes (not shown), that are connected by a wire 109, forming a biomedical sensor 108 that produces a heart-related signal 110. The wrist bands 106a and 106b, respective electrodes, and connecting by the wire 109 disposed therebetween, form one example of an ECG sensor. It should be understood that the ECG sensor may be any suitable ECG sensor, module, or system, that outputs the heart-related signal 110. Further, an electrode may be any suitable electrode, such as the CB electrode, disclosed above.

The heart-related signal 110 that is produced by the biomedical sensor 108 includes motion artifacts that are signal artifacts produced by movement of the biomedical sensor 108 relative to a sensing location (not shown). The sensing location may be a skin surface of an area on the subject's wrist where the wrist band 106a or 106b is worn, or any other suitable sensing location, such as a chest, at which the biomedical sensor 108 senses the heart-related signal 110.

It should be understood that a subject referred to herein may be any living being, such as a person or an animal, and may be referred to interchangeably herein as a user or a patient. Further, movement of the biomedical sensor 108 relative to the sensing location may be caused by any suitable source of the movement that causes movement of the biomedical sensor 108 relative to the sensing location, such as vibration experienced during ambulatory transport of the patient to a hospital. Further the heart-related signal 110 may be one or more heart-related signals which in combination, form a heart-related signal.

Physical activity of the subject 102 may cause movement of the wrist band 106a or 106b, and, thus, movement of the biomedical sensor 108, such as relative movement of one or more of the electrodes at respective sensing locations, such as the skin on the subject 102's left and right wrist, resulting in a charge deformation at the electrode-skin boundary. As such, strenuous and high intensity exercise of the subject 102, such as running or any other suitable activity, such as riding in an ambulance, may result in movement that rises to a level causing motion artifacts in the heart-related signal 110.

According to embodiments disclosed herein, the heart-related signal 110 may be reconstructed 112, producing a reconstructed heart-related signal with the motion artifacts suppressed 114. The reconstructed heart-related signal with the motion artifacts suppressed 114 may be used to accurately estimate HR, HRV, or any other suitable heart-related estimate. As such, the reconstructed heart-related signal may be employed to detect or predict a heart-related ailment. The heart-related ailment may include at least one of a heart rate variability (HRV) condition, atrial fibrillation condition, congestive heart failure condition, and tachycardia condition.

Figure 1B:
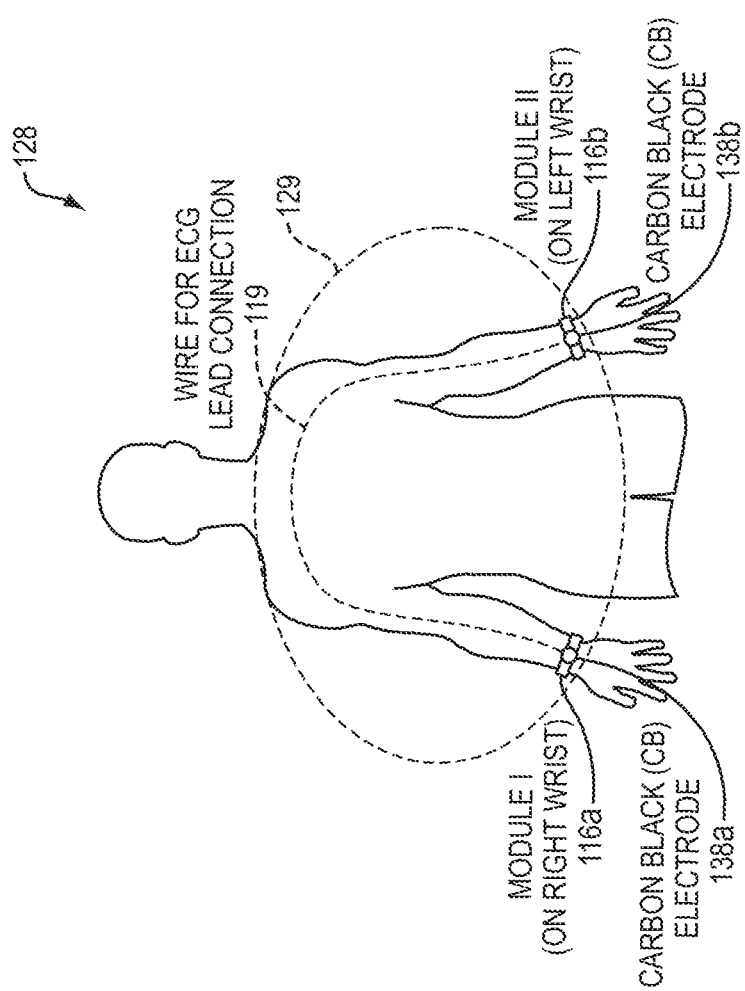
FIG. 1B is a block diagram of an example electrocardiogram (ECG) wearable sensor.

FIG. 1B is a block diagram 128 of an example electrocardiogram (ECG) wearable sensor 129 that may be employed as the biomedical sensor 108 of FIG. 1A. The ECG wearable sensor 129 comprises a first module 116a and a second module 116b including a first CB electrode 138a and a second CB electrode 138b, respectively. The first CB electrode 138a and the second CB electrode 138b are connected by a wire 119.

Figure 2A:
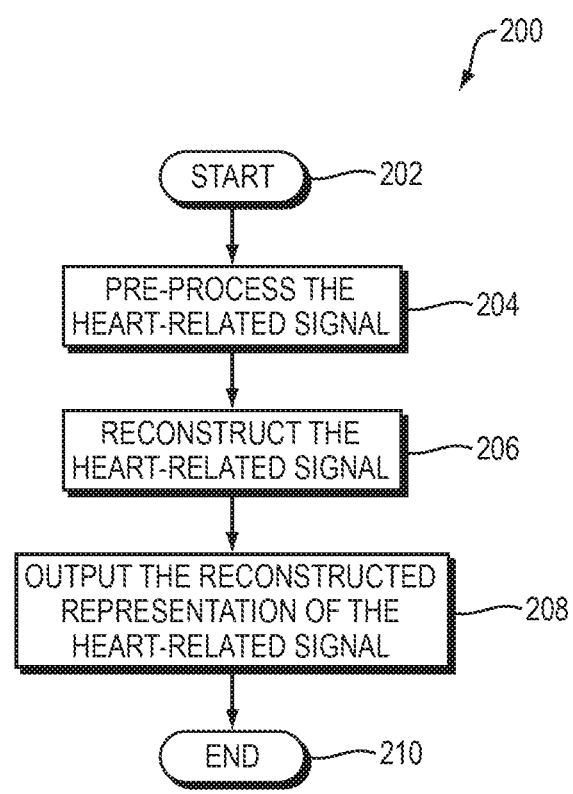

FIG. 2A is a flow diagram 200 of an example embodiment of a method for reconstructing a heart-related signal output by a biomedical sensor. The method may start (202) and pre-process (also referred to interchangeably herein as pre-process) the heart-related signal to produce a pre-processed heart-related signal (204). The method may reconstruct a representation of the heart-related signal to produce a reconstructed representation of the heart-related signal based on a time-varying spectral analysis of the pre-processed heart-related signal, the heart-related signal including motion artifacts (206). The motion artifacts may be signal artifacts produced by movement of the biomedical sensor relative to a sensing location. The pre-processing may reduce the motion artifacts in the pre-processed heart-related signal for the reconstructing. The method may output the reconstructed representation of the heart-related signal (208) and the method thereafter ends (210) in the example embodiment.

FIG. 2B is a flow diagram of an another example embodiment of a method for reconstructing a heart-related signal output by a biomedical sensor. The method corresponds to Stage 1 (ECG pre-processing), Stage 2 (time-varying spectral analysis), Stage 3 (spectral filtering) and Stage 4 (HR Tracking and Extraction from ECG Spectrum) of Table 1, disclosed below, for reconstructing a heart-related signal output by a biomedical sensor.

TABLE 1

SegMA method: HR and ECG signal reconstruction

Stage 1. ECG Preprocessing
   1.1. Down sample the ECG to ¼ of the original sampling rate
   1.2. Compute the derivative of downsampled ECG signal.
   1.3. Take an absolute value of the derivative (optional)
Stage 2. Time-Varying Spectral analysis
   2.1. Compute the power spectral density of preprocessed ECG data at each time window of 8 sec
Stage 3. Spectral Filtering
   3.1. Assume HR to be in the frequency range of [0.5 Hz-3 Hz], this accounts for both low and high heart rates.
   3.2. The first highest two peaks and their corresponding frequencies in the ECG filtered spectrum are assumed to have HR information.
Stage 4. Heart Rate Tracking and Extraction from ECG Spectrum
   Case (1): if the spectrum is corrupted by movement and only the first largest peak is corrupted, then the HR frequency should be the frequency of the second peak in the spectrum.
   Case (2): Due to skin-electrode interface changes, the HR frequency cannot be extracted from the spectrum and in this case the previous HR frequency is used or for offline implementation a cubic spline interpolation can be applied to fill in the missing HR information.
Stage 5. Heart Rate Variability Analysis
   By using a sample-by-sample windowing strategy, beat-to-beat HR can be extracted, from which dynamics of heart rate variability analysis can be obtained on the SegMA reconstructed HR time series.

The method may start (222) with a first windowed segment window [k] of raw ECG data (224). The raw ECG data (224) may be extracted from a heart-related signal that is output by an ECG sensor in any suitable way. The raw ECG data (224) may be extracted in real-time or non-real-time (e.g., from a database).

The method may pre-process the ECG signal (226) (see Table 1, Stage 1, ECG Pre-processing) to produce a pre-processed heart-related signal. The pre-processing (226) may include down-sampling the heart-related signal to produce a down-sampled heart-related signal, the down-sampling being at a sampling rate less than an original sampling rate (e.g., ¼ of the original sampling rate). This may improve a frequency resolution in a time-frequency spectrum of the ECG employed by the restructuring, as disclosed below. The pre-processing (226) may include computing a derivative of the down-sampled heart-related signal to reduce the motion artifacts, as the derivative may accentuate peaks of the ECG. The motion artifacts can be reduced to some extent via the derivative as long as the motion is not abrupt and the samples are uniformly corrupted by the movement. The pre-processing may further include computing an absolute value of the derivative to further reduce the motion artifacts by further accentuating the peaks of the ECG. As such, the pre-processing may reduce the motion artifacts in the pre-processed heart-related signal for the restructuring.

The method may include computing a time-frequency spectrum (TFS) (see Table 1, Stage 2, Time Varying Spectral Analysis) of the pre-processed heart-related signal (228). The TFS computed may be a 3-dimensional spectra including a time-varying amplitude or power distribution with respect to time and frequency, such as a time-varying power spectral density (PSD). Any suitable time-frequency technique may be employed, such as a variable frequency complex demodulation (VFCDM), disclosed in U.S. Pat.

No. 8,388,543 B2, incorporated herein in its entirety by reference, smoothed pseudo wigner-ville method, or a wavelet based method.

The method may further include limiting the TFS computed to a given frequency range (see Table 1, Spectral Filtering). The given frequency range may be 0.5 Hz to 3 Hz to account for both low and high heart rates. The HR estimation may be based on a strategy that eliminates (i.e., discards) frequencies that are outside of this HR range as they are most likely due to motion artifacts or harmonics of the HR frequency. As such, this is one aspect in which the reconstructing may further reduce the motion artifacts reduced by the pre-processing.

Figure 8A:
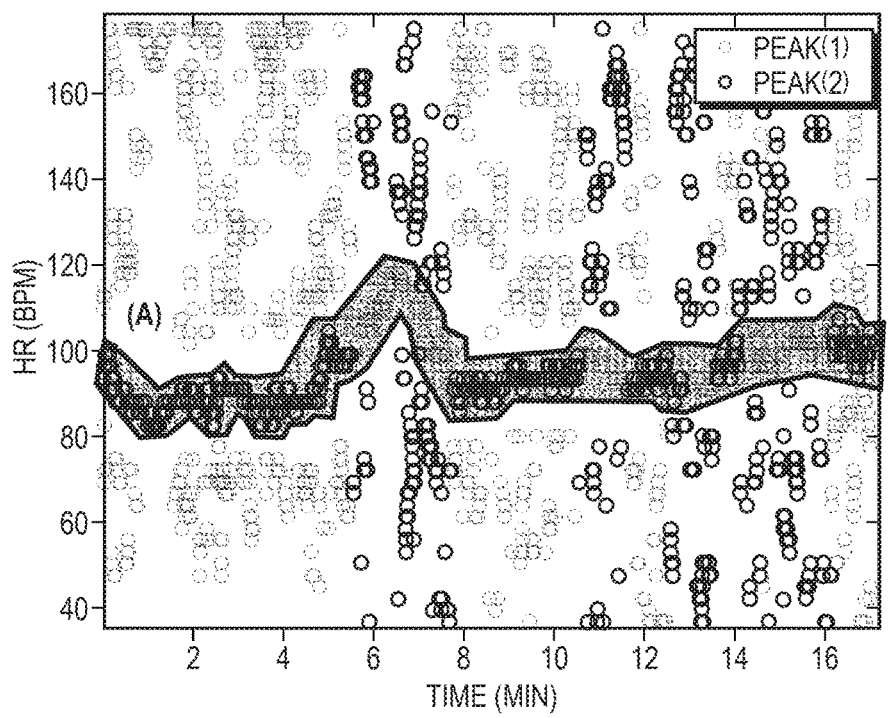
FIG. 8A is a plot of another ECG time-frequency spectrum.

Based on an assumption that the HR frequency component is a dominant peak (i.e., peak having highest power or amplitude relative to other peaks at a time point) in the PSD window k of a clean ECG signal, the filtered time-frequency spectrum using the first N (e.g., two) largest peaks of PSD at each window k can be extracted (230), as shown in FIG. 8A, disclosed below. The method may check (232) if there are any peaks in the spectrum. If not (see Table 1, Heart Rate Tracking and Extraction from ECG, Case (2)), the reconstructed representation HR(k) (234) may be set to a previous reconstructed representation HR(k-1) (or a moving average of several past HR beats or some other variant) a for real-time implementation; alternatively, an offline implementation may be used, such as a cubic spline interpolation that can be applied to fill in the missing HR information, and the method thereafter ends (242) in the example embodiment.

If there is a peak present (232), up to a pre-determined number N of frequency spectra (also referred to interchangeably herein as frequency components) may be retained to produce a subset of frequency spectra, such as Peak 1 and Peak 2 shown in FIG. 8A, disclosed below. The method may select a spectral peak for the reconstructing. The selected spectral peak may be selected from amongst spectral peaks of the subset (e.g., the peaks i=1 . . . N) of the frequency spectra and a previous frequency component, such as HR(k-1) (or a moving average of several past HR beats or some other variant). The previous frequency component may have been selected for a previous shift, such as k-1. It should be understood that the spectral peak is being selected for a point in time in the time-frequency spectrum. For example, it should be understood that the two peaks, Peak 1 and Peak 2, are being tracked at each point in time in the time-frequency spectrum shown in FIG. 8A, disclosed below.

For a case in which the windowed ECG signal is clean, the first highest peak in the spectrum may represent the HR fundamental frequency. For a case in which the windowed ECG signal is corrupted by movement and the second peak corresponds to HR, while the HR spectral peak may be detectable, the difference between its value and that of the previous HR, for example, HR(k-1), may be more than a given difference value (also referred to interchangeably herein as distance value), such as 10 beats-per-minute (bpm) or 15 bpm, or any other suitable difference value. As such, it may be replaced by the most recent HR value from a previous window segment (or a moving average of several past HR beats or some other variant).

According to some embodiments, a criterion may be set that the HR value cannot change more than the given difference value, such as 15 bpm, or any other suitable value, from a previous time window. A respective difference value may be computed (236) for each spectral peak in the subset and each respective difference may be checked (238) to select from amongst the subset (e.g., the peaks i=1 . . . N) or the previous HR(k-1). For example, if none of the spectral peaks meet the criterion checked (238), the previous HR(k-1) may be selected (234) and the method thereafter ends (242) in the example embodiment. If, however, one or more spectral peaks in the subset do meet the criterion, a spectral peak having a smallest difference value may be selected (240) and the method thereafter ends (242) in the example embodiment. It should be understood that the TFS may be computed for each shift k of a windowed data segment window(k) of the heart-related signal that is pre-processed (226) and that the heart related signal may be reconstructed for each shift k of the windowed data segment window(k).

Figure 8B:
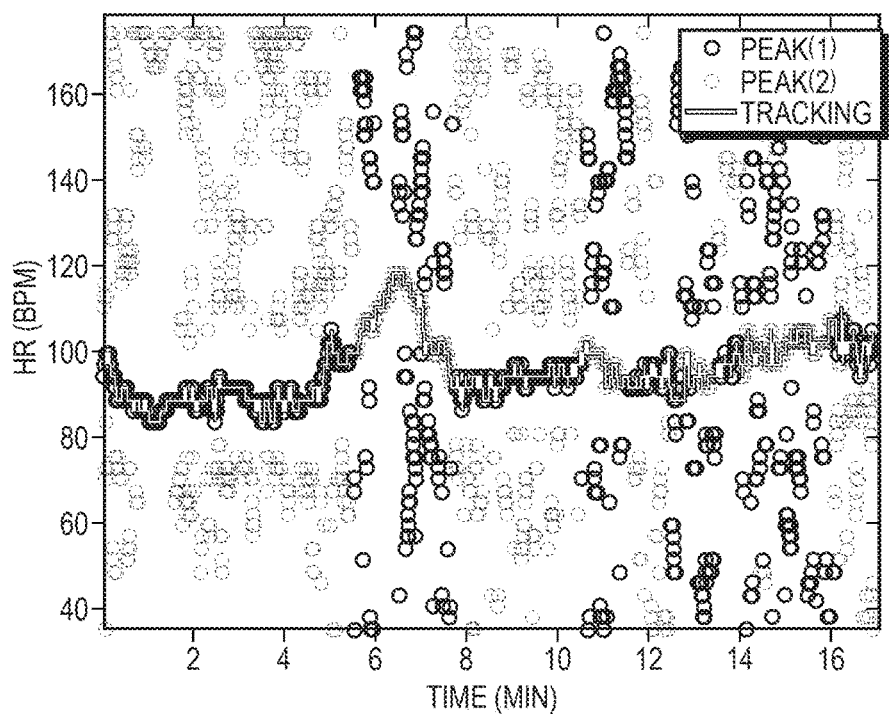
FIG. 8B is a plot showing tracking of an HR trace in the ECG spectrum of FIG. 8A.

It can be observed from FIG. 8B, disclosed below, that in most cases, the blue circle which represents the largest spectral peak is chosen (i.e., selected, extracted); however, in other cases, green circles are chosen for certain time points. For the HR peaks associated with the green circles, they are chosen because either the first highest peak is related to a motion artifact or the highest magnitude peak deviates more than the given difference value, such as 15 bpm, from the previous HR value. As such, another aspect in which the reconstructing may further reduce the motion artifacts reduced by the pre-processing may result based on the particular spectral peak that is chosen for a time point.

The method may employ the reconstructed representation to determine a heart rate variability (HRV) estimate, as disclosed Stage 5, Heart Rate Variability Analysis, of Table 1, disclosed above. The method may employ the reconstructed representation to determine a heart rate estimate. The method may employ the reconstructed representation to detect or predict a heart-related ailment. The heart-related ailment may include at least one of a heart rate variability (HRV) condition, atrial fibrillation condition, congestive heart failure condition, and tachycardia condition.

According to some embodiments, the SegMA method may reduce motion artifacts by employing a motion signal from a motion sensor. The heart-related signal and the motion signal may be produced, concurrently. The method may further comprise segmenting the heart-related signal into a plurality of windowed heart-related signal data segments and the motion signal into a corresponding plurality of windowed motion signal data segments and repeating the pre-processing, the reconstructing, and the outputting for each windowed heart-related signal data segment and each corresponding motion signal data segment. The time window may be a value in a range from 2 to 32 seconds. For example, the window[k] of raw ECG data of FIG. 3A, element 304, disclosed below, and the window[k] of raw accelerometer data shown in FIG. 3A, element 310, disclosed below, may each include data from the respective ECG and accelerometer signals that may be collected over a time window from 2 to 32 seconds. According to one embodiment, the time window may be 8 seconds.

According to some embodiments, the biomedical sensor may be an ECG sensor. The motion sensor may be an accelerometer, or any other suitable device that produces a motion signal. If an accelerometer, the accelerometer may be a 3-axial type accelerometer, or any other suitable type of accelerometer. The biomedical sensor and the motion sensor may be co-located. For example, the wrist bands 106*a* and 106*b* of FIG. 1A, disclosed above, may be smartwatches and the biomedical sensor and motion sensor may be an ECG sensor and an accelerometer, respectively, that are both disposed in each smartwatch or other suitable wearable device.

For a SegMA method employing the motion signal, the time-varying spectral analysis may be a first time-varying spectral analysis. The reconstructing may be further based on a second time-varying spectral analysis of a motion sensor based on embodiments disclosed in Tables 2-4, disclosed below.

TABLE 2

Stages 1 and 2

Stage 1. Time-Varying Spectral analysis (see FIG. 3A)
   1.1. Filter the ECG and Accelerometer signal with cutoff frequency [1, 50]/Fs/2 Hz.
   1.2. Down sample the ECG and Accelerometer signal to ¼ of original sampling rate (Fs).
   1.3 Compute the derivative of the ECG and an absolute value (optional) of the derivative
   1.3. Compute the time frequency spectrum of both ECG and Accelerometers [0-10 Hz].
Stage 2. Movement Classification (see FIG. 3A)
   2.1. Check each accelerometer (X, Y or Z) amplitude modulation at each window and compare to a pre-defined motion amplitude threshold. (The threshold varies depending on the type of accelerometer sensor).
   Signal is clean if $AM[Acc_{x\ or\ y\ or\ z}(k)]$ < Motion_Threshold and the signal is corrupted by motion otherwise. If the signal is clean calculate the Heart Rate from peak-to-peak intervals, otherwise go to step 2.2.
   2.2. If the signal is corrupted check if the movement is pseudo-periodic (e.g. during walk, jog, run) or non-periodic (e.g. any random movements)
   The assumption is when movement is pseudo-periodic the accelerometer data should comprised of a fundamental frequency component and harmonics of the fundamental frequency at its double and third frequency band. This means the ratio of the first harmonic to the fundamental frequency should be almost 2 and the second harmonic to the fundamental should be around 3.
      2.2.1. Extract the fundamental frequency component, the $1^{st}$ and $2^{nd}$ harmonics from (e.g., VFCDM) time-frequency spectrum of accelerometers. The first three highest peaks in spectral array should represent the fundamental, $1^{st}$ and $2^{nd}$ harmonics as long as the movement is pseudo-periodic.
      2.2.2. Calculate the ratio of the extracted 1st and 2nd fundamental frequency to the extracted fundamental frequency. If the ratios are close to 2 and 3, this indicates that the movement is most likely pseudo-periodic otherwise it is non-periodic.
      2.2.3. If the movement is pseudo-periodic do the Stages 3-5 (See Table 2 and FIG. 3B), otherwise go to Stage 6 (See Table 3 and FIG. 3C).

TABLE 3

Stages 3-5

Stage 3. Spectral Filtering (see FIG. 3B)
   3.1. Assume HR to be in the frequency range of [0.5 Hz-3 Hz], this accounts for both low and high heart rates.
   3.2. The first highest (e.g., three peaks) and their corresponding frequencies in the ECG filtered spectrum are assumed to have HR information.
   3.3. Only the largest frequency peak (that represents the fundamental frequency of movement) of the accelerometers' spectra is used for motion artifact detection in Stage 4.
Stage 4. Motion Artifact Detection (see FIG. 3B)
   4.1. Compare the frequencies of the three peaks in the ECG spectrum with the frequency of the largest peak in the accelerometers' spectra. If the first or second largest peaks in the ECG spectrum are similar to that of the accelerometers' peaks, then motion artifact is present in the ECG.
   4.2. If motion artifact is detected from 3.1, then the corresponding frequency peak (usually the first or second largest peak) in the ECG spectrum should be discarded.
Stage 5. Heart Rate Tracking and Extraction from ECG Spectrum (see FIG. 3B)
   Case (1): From 3.1—if the spectrum is corrupted by movement and only the first largest peak is corrupted, then the HR frequency should be the frequency of the second peak in the spectrum.
   Case (2): From 3.1—if the spectrum is corrupted by movement and both the first and second largest peaks have similar frequencies to those of the accelerometers' peaks, then the HR frequency should be the frequency of the third peak in the spectrum.
   Case (3): Due to a gap between the pulse oximeter and a subject's skin, the HR frequency cannot be extracted from the spectrum and in this case the previous HR frequency is used or for offline implementation a cubic spline interpolation can be applied to fill in the missing HR information.

signal, the motion signal output by a motion sensor and representative of the motion artifacts in the heart-related signal. The method may further include employing the second time-varying spectral analysis of the motion signal to produce a movement classification of the movement, and wherein the reconstructing is further based on the classification of the movement.

Figure 3A:
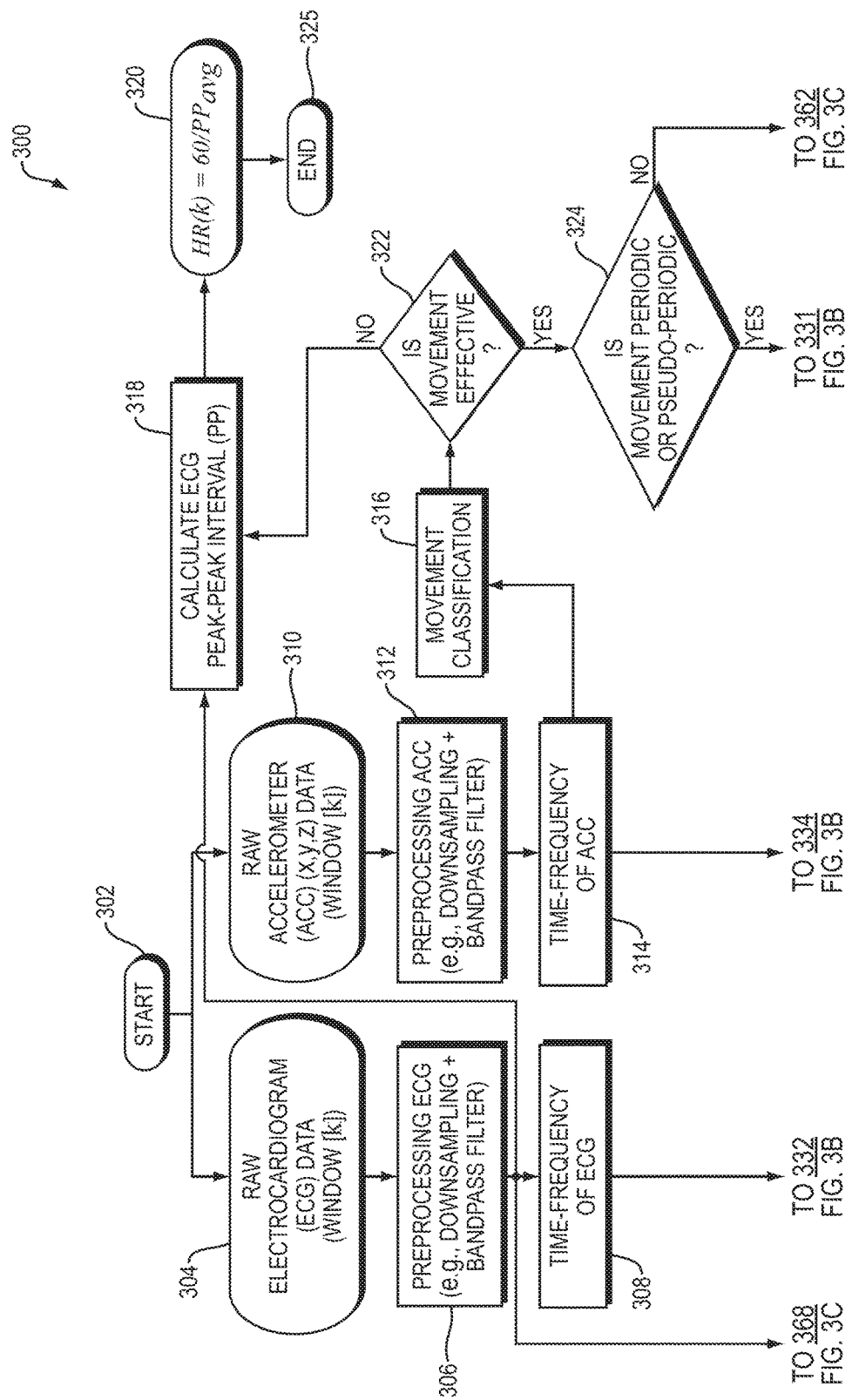
Figure 3B:
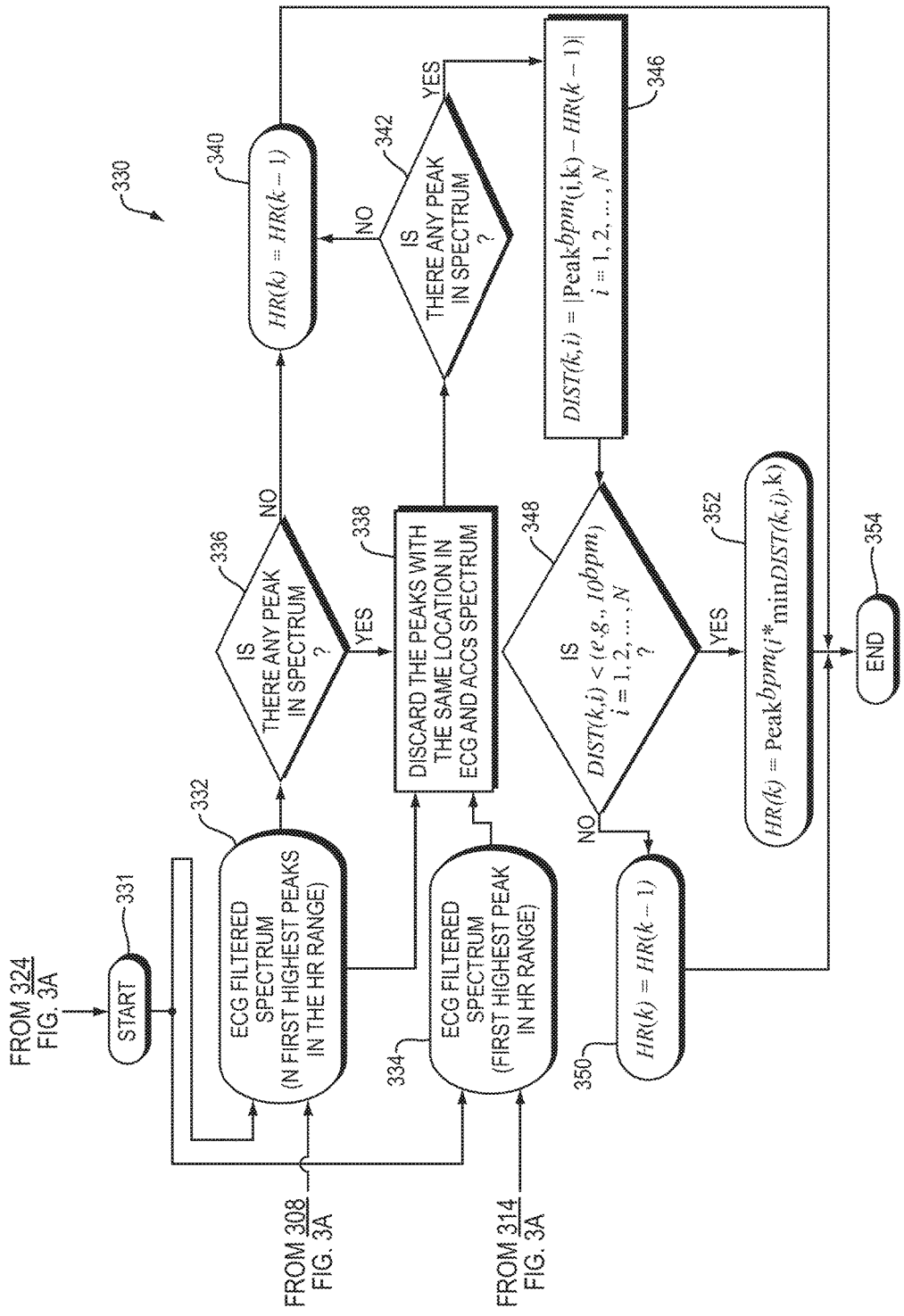

FIGS. 3A-C are flow diagrams of example embodiments of a SegMA method employing the motion signal for reconstructing a heart-related signal output by a biomedical

TABLE 4

Stage 6

| Stage 6. | Adaptive Bandpass Filtering (non-periodic movements) (see FIG. 3C) When the movement is random and non-periodic it is difficult or not possible to identify HR trace from time-frequency spectrum (for example if stage 5 is not applicable). In this case which may happen more often, a new procedure is adopted that is called adaptive bandpass |
|---|---|

TABLE 4-continued

Stage 6 filtering. The assumption here is that HR does not deviate more than 10 bpm from the average of previous m HR values within 2 seconds.

6.1. Set averaging window length to m (e.g. m = 5) and calculate the average of recent m estimated HR values.

$$HR_{mavg} = \frac{1}{m}\sum_{j=1}^{m} HR(k-j)$$

Where k is the current window. The window length m = 5 should only be used for up to 10 seconds of consecutive motion artifact corrupted datapoints. If motion corrupted data last more than 10 seconds, m should be increased to more than 5.

6.2. Take the most recent estimated HR value and calculate bandpass filter cutoff frequency.

$F_{CutOff} = [HR_{mavg} - 10, HR_{mavg} + 10]/60/Fs/2$

Design a bandpass filter of order 4 with cutoff frequency ($F_{cutoff}$). Apply the filter on the ECG segment.

6.3. Calculate HR from peak-to-peak intervals of the filtered data segment obtained from 6.2. Take the average of the instantaneous HR as estimated HR value at window k.

FIG. 3A is a flow diagram (300) of an example embodiment of a method for a time-varying spectral analysis and movement classification, as disclosed in Stage 1 (time-varying spectral analysis) and Stage 2 (movement classification), respectively, in Table 2, for reconstructing the representation. The method may start (302) and the time-varying spectral analysis may be employed on a first windowed segment window [k] of raw ECG data (304) and a second windowed segment window [k] of raw accelerometer (ACC) data (310). The raw ECG data (304) and the raw ACC data (310) may be extracted from a heart-related signal that is an ECG signal and a motion signal that is an accelerometer signal, respectively.

As disclosed in Stage 1 of Table 2, the time-varying spectral analysis of FIG. 3A may include pre-processing the heart-related signal (306) to produce a pre-processed heart-related signal. The pre-processing (306) may include filtering the heart-related signal to produce a filtered heart-related signal. The pre-processing (306) may further include down-sampling the filtered heart-related signal, the down-sampling being at a sampling rate less than an original sampling rate, to produce a down-sampled, filtered heart-rate signal. The pre-processing may include computing a derivative of the down-sampled heart-related signal to reduce the motion artifacts. The pre-processing may further include computing an absolute value of the derivative to further reduce the motion artifacts.

The time-varying spectral analysis may further include pre-processing the motion signal (312) to produce a pre-processed motion signal. The pre-processing (312) may include filtering the motion signal to produce a filtered motion signal. The pre-processing (312) may further include down-sampling the filtered motion signal, the down-sampling being at a sampling rate less than an original sampling rate, to produce a down-sampled, filtered motion signal.

As further disclosed in Stage 1 of Table 2, the time-varying spectral analysis of FIG. 3A may include computing a first time-frequency spectrum (TFS) to produce a first TFS (308) of the down-sampled, filtered heart-related signal and computing a second TFS to produce a second TFS (314) of the down-sampled, filtered motion signal. According to some embodiments, filtering and down-sampling of the heart-related signal and motion signal for computing the first TFS (308) and the second TFS (314), respectively, may be optional. The first TFS (308) (also referred to interchangeably herein as the first TFS computed) and the second TFS (314) (also referred to interchangeably herein as the second TFS computed) may be 3-dimensional spectra, the first TFS computed and the second TFS computed each including a respective time-varying amplitude or power distribution with respect to time and frequency.

For example, the first TFS computed may be a first time-varying power spectral density (PSD) and the second TFS computed may be a second time-varying PSD. A time-frequency technique, such as a variable frequency complex demodulation (VFCDM), disclosed in U.S. Pat. No. 8,388,543 B2, incorporated herein in its entirety by reference, may be used for computing the first TFS (308), that is, a TFS of the ECG signal, and the second TFS (314), that is, a TFS of the accelerometer signal. However, it should be understood that any suitable time-frequency technique may be used, such as a smoothed pseudo wigner-ville method, or a wavelet based method.

As disclosed in Stage 2 of Table 2, classifying the classification of the movement (316) in FIG. 3A may include comparing an amount of amplitude modulation in the second TFS (314) computed to an amplitude modulation threshold. The amplitude modulation threshold may be dependent on a type of the motion detector sensor, such as a type of the accelerometer. The classification of the movement may indicate whether the movement rises to a level causing motion artifacts in the heart-related signal, that is, the ECG signal, based on a result of the comparing, as disclosed in Stage 2 of Table 2.

In an event the movement classification (316) of FIG. 3A indicates that the movement does not rise to a level causing the motion artifacts (322), a peak-peak interval (PP) of the filtered heart-related signal, or alternatively, the filtered, down-sampled heart-rate signal, may be computed (318) and the reconstructed representation HR(k) may be based on an average value of peak-to-peak intervals (320) in the pre-processed heart-related signal, and the method thereafter ends (325) in the example embodiment.

In an event the movement classification (316) indicates that the movement does rise to the level causing the motion artifacts (323), classifying the classification of the movement may further include determining (324) whether the movement is either a pseudo-periodic movement or a periodic movement, versus a random movement, as disclosed in Stage 2 of Table 2.

With reference to Stage 2 of Table 2, in determining whether the movement is either the pseudo-periodic movement or the periodic movement, versus the random movement, the method may further include identifying a first, second, and third frequency associated, respectively, with a first, second, and third spectral peak in the second TFS at a point in time in the second TFS. The first, second, and third peaks may have largest power or amplitude values relative to other peaks in the second TFS at the point in time. The first spectral peak may be a largest spectral peak amongst the first, second, and third spectral peaks.

In determining whether the movement is either the pseudo-periodic movement or the periodic movement, versus the random movement, the method may compute a first ratio of the second frequency identified to the first frequency identified. The method may determine a first comparison result by comparing the first ratio computed to a first ratio value. The method may compute a second ratio of the third frequency identified to the first frequency identified and determine a second comparison result by comparing the second ratio computed to a second ratio value. The classification may further indicate the movement is either the pseudo-periodic movement or the periodic movement, versus the random movement, based on the first comparison result and the second comparison result. The first ratio value may be 2 and the second ratio value may be 3. The classification of the movement may be periodic if the first ratio and the second ratio are exactly 2 and 3, respectively, while the classification of the movement may be pseudo-periodic if the first ratio and the second ratio are approximately 2 and 3, respectively, within a pre-determined level of accuracy.

In an event the classification of the movement is periodic or pseudo-periodic, the method of FIG. 3A may continue with the method of FIG. 3B, disclosed below. In an event the classification of the movement is random, the method of FIG. 3A continues to the method of FIG. 3C, disclosed below.

FIG. 3B is a flow diagram (330) of an example embodiment of a method for spectral filtering, motion artifact detection, and heart rate tracking and extraction, as disclosed in Stages 3, 4, and 5, respectively, of Table 3, for reconstructing the representation. The reconstructed representation may be referred to herein as a current reconstructed representation or HR(k). As disclosed above with regard to FIG. 3A, in an event the classification of the movement (316) is periodic or pseudo-periodic, the method of FIG. 3A may continue with the method of FIG. 3B.

The method of FIG. 3B may start (331) and retain (332) up to a pre-determined number N of candidate spectral peaks located at a first point in time in the first TFS, that is, the first TFS from FIG. 3A. It should be understood that the method of FIG. 3B may be performed for each point in time of the first TFS and the second TFS. According to one embodiment, the pre-determined number N may be 2 or 3. The candidate spectral peaks retained may be based on having corresponding frequencies within a given frequency range. The candidate spectral peaks may be N peaks in the given frequency range that have highest amplitude or power values relative to other spectral peaks, that is, the first N highest peaks. It should be understood that the other spectral peaks have respective frequencies also within the given frequency range and are peaks located at the first point in time in the first TFS. The given frequency range may be 0.5 Hz to 3 Hz. As such, the N first highest peak in the range 0.5 Hz to 3 Hz in the first TFS may be retained at the first time point. Since no peaks in the given frequency range may be present at the first time point, the method may determine (336) whether at least one spectral peak is present.

Based on the determination (336) that no peak is present, the current reconstructed representation HR(k) may be based on a prior reconstructed representation HR(k-1) (340), the prior reconstructed representation HR(k-1) associated with a previous point in time, such as the previous window k-1, in the first TFS computed, and the method thereafter ends (354) in the example embodiment.

Based on a determination (336) that the at least one spectral peak is present, the method may discard (338) each of the candidate spectral peaks retained, that is, each peak of the N first highest peaks determined at (332), if the peak is associated with a same frequency as a dominant spectral peak located at a second point in time in the second TFS (314) computed as disclosed above with regard to FIG. 3A. The first point in time and the second point in time may have same time values. The dominant spectral peak may have a largest power or amplitude value relative to other peaks located at the second point in time in the second TFS. The method may determine (342) whether any peaks are retained after the discarding (338). The discarding (338) may be referred to herein as a first discarding.

In an event the discarding (338) discards each of the candidate spectral peaks retained, reconstructing the current representation HR(k) may be based on the prior reconstructed representation, HR(k-1) (340), and the method thereafter ends (354) in the example embodiment.

In an event the first discarding (338) results in at least one remaining candidate spectral peak retained, reconstructing the current representation may further include second discarding (348). The second discarding (348) may discard remaining candidate spectral peaks, of the at least one remaining candidate spectral peak retained, based on whether a corresponding frequency of the at least one remaining candidate spectral peak retained is distanced (346) by at least a frequency difference threshold, such as 10 bpm, from a prior reconstructed representation's frequency, that is, a frequency associated with, for example, HR(k-1).

Based on each at least one remaining candidate spectral peak retained having been discarded by the second discarding (348), reconstructing the current representation may be based on the prior reconstructed representation HR(k-1) (350), and the method thereafter ends (354) in the example embodiment.

Based on at least one last candidate spectral peak remaining from the second discarding (348), reconstructing the current representation may be based on a selected candidate spectral peak (352). The selected candidate spectral peak may be selected from amongst the at least one last candidate spectral peak remaining having a closest corresponding frequency to the prior reconstructed representation's frequency relative to respective frequencies of each of the at least one last candidate spectral peak remaining, and the method thereafter ends (354) in the example embodiment.

As disclosed above with regard to FIG. 3A, in an event the classification of the movement (316) is random, the method of FIG. 3A may continue with the method of FIG. 3C.

FIG. 3C is a flow diagram (330) of an example embodiment of a method for adaptive bandpass filtering of non-periodic movements, that is, random movements, for reconstructing the representation, as disclosed in Stage 6 of Table 4. The method of FIG. 3C may start (362) and compute an average value of a number m of prior reconstructed representations outputted prior to the reconstructing (362). The number m may be based on a duration of consecutive motion artifacts, detected prior to the reconstructing of the representation HR(k). For example, if motion artifacts were detected for windows k-1, k-2, and k-3, m may be understood to be 3.

The method may compute a bandpass filter cutoff frequency (366). The cutoff frequency $F_c$ may be based on the average value computed $HR_{mavg}$. The method may filter the pre-processed heart-rate signal (306), disclosed in FIG. 3A, above, by applying the band pass filter computed (368) to produce a filtered, pre-processed heart-related signal. The reconstructed representation HR(k) may be based on an average peak-to-peak interval value (372) of the filtered, pre-processed heart-rate signal, and the method thereafter ends (374) in the example embodiment.

Figure 4:
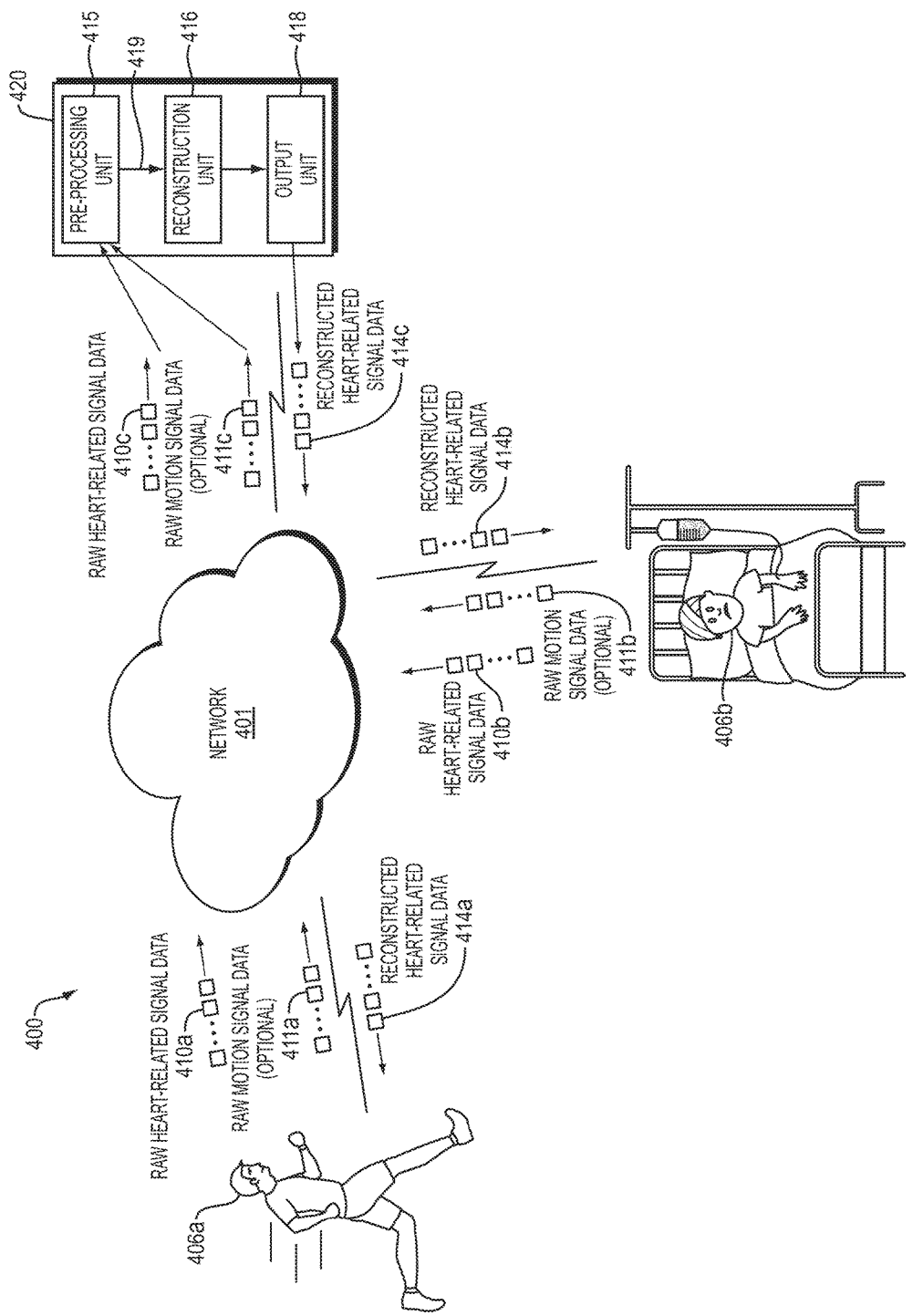
FIG. 4 is a block diagram of an example embodiment of a system.

FIG. 4 is a block diagram of an example embodiment of a system (400). The system includes an apparatus 420 for reconstructing a heart-related signal 410c output by a biomedical sensor (not shown). The apparatus 420 includes a pre-processing unit 415, a reconstruction unit 416, and an output unit 418. The pre-processing unit 415 may be configured to pre-process the heart-related signal 410c to produce a pre-processed heart-related signal 419. The reconstruction unit 416 may be configured to reconstruct a representation of the heart-related signal 410c to produce a reconstructed representation of the heart-related signal 414c. The reconstructing may be based on a time-varying spectral analysis of the pre-processed heart-related signal 419.

The heart-related signal 410c may include motion artifacts, the motion artifacts being signal artifacts produced by movement of a biomedical sensor (not shown) relative to a sensing location (not shown). The pre-processing unit 415 may reduce the motion artifacts in the pre-processed heart-related signal 419 for the reconstructing by the reconstruction unit 416. The reconstruction unit 416 may further reduce the motion artifacts reduced by the pre-processing unit 415. The output unit 418 may be configured to output the reconstructed representation of heart-related signal 414c.

The apparatus 420 may be communicatively coupled to a network 401 to receive the heart related signal 410c and, optionally, a motion signal 411c. The motion signal 411c (optional) may be output by a motion sensor (not shown) and representative of motion artifacts in the heart-related signal 410c.

The network may be a wireless network or any other suitable network. The pre-processing, the reconstructing, and the outputting may be performed in near real-time with respect to production of the heart-related signal 410c and, optionally, the motion signal 411c. Alternatively, the apparatus may be coupled to a database (not shown) storing representations of the heart related signal 410c and, optionally, the motion signal 411c, and the pre-processing, the reconstructing, and the outputting may be performed in non-real-time with respect to production of the heart-related signal 410c and the motion signal 414c.

The heart-related signal 410c may include raw heart-related signal data that includes the raw heart-related signal data 410a and the raw heart-related signal data 410b output by biometric sensors (not shown) that sense the heart-related signal data 410a and the raw heart-related signal data 410b from sensing locations (not shown) on a first user 406a and a second user 406b, respectively. The motion signal 411c (optional) may include raw motion signal data that includes the raw motion signal data 411a (optional) and the raw motion signal data 411b (optional) from the motion sensors (not shown). The raw motion signal data 411a (optional) and the raw motion signal data 411b (optional) may represent motion artifacts in the heart-related signal data 410a and the raw heart-related signal data 410b, respectively.

It should be understood that the raw heart-related signal data 410a-b and, optionally, the raw motion signal data 411a-b, may be sent to the apparatus 420 in any suitable way. For example, the raw heart-related signal data 410a and the raw motion signal data 411a (optional) may be sent in a payload of a packet; alternatively the raw heart-related signal data 410a and the raw motion signal data 411a (optional) may be sent in payloads of different packets. Similarly, the raw heart-related signal data 410b and the raw motion signal data 411b (optional) may be sent in a payload of a packet; alternatively, the raw heart-related signal data 410b and the raw motion signal data 411b (optional) may be sent in payloads of different packets.

The user 406a may be at a gym where the user 406a is exercising, and such physical activity by the user 406a may cause motion artifacts in the raw heart-related signal data 410a. The user 406b may be in a different location, such as a hospital. The user 406b may perform movements out of boredom, such as wrist shaking, causing motion artifacts in the raw heart-related signal data 410b. As such, the corresponding motion artifacts may be suppressed (i.e., reduced, mitigated) in the reconstructed representations 414a and 414b of the heart-related signals 414a and 414b, respectively, according to embodiments disclosed herein. The reconstructed representations 414a and 414b, or information derived therefrom, may be sent to biometric devices or other devices communicatively coupled to the network 401 and the user, such as the user 406a or 406b may have access to such devices. Alternatively, the reconstructed representations 414a and 414b, or information derived therefrom, may be sent in any suitable manner to another device communicatively coupled to the network 401 such that the reconstructed representations 414a and 414b, or information derived therefrom, may be accessible to a third party, such as doctor, or any other suitable party.

Figure 5:
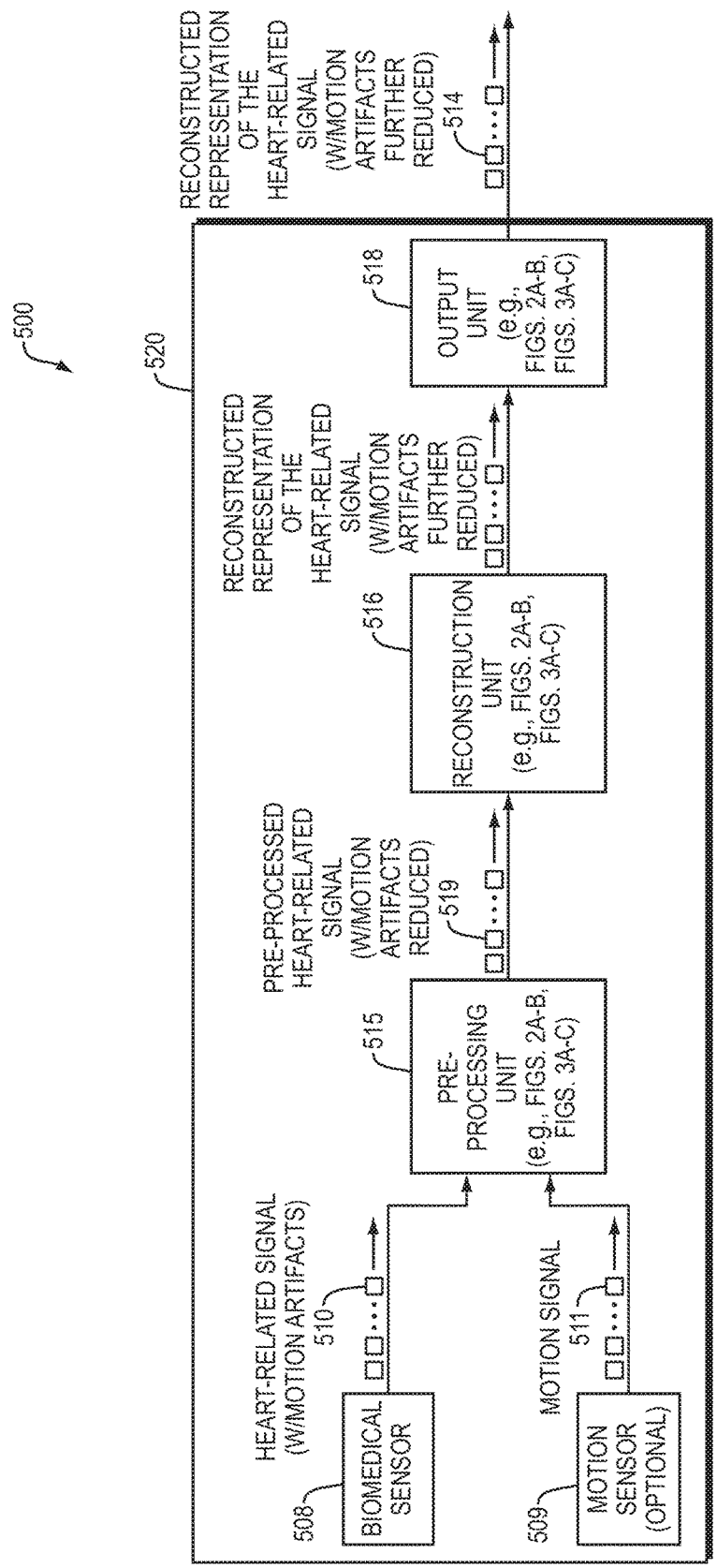
FIG. 5 is a block diagram of an example embodiment of an apparatus for reconstructing a heart-related signal output by a biomedical sensor.

FIG. 5 is a block diagram 500 of an example embodiment of an apparatus (520) for reconstructing a heart-related signal 510 output by a biomedical sensor 508. The apparatus 520 includes a pre-processing unit 515 configured to pre-process the heart-related signal 510 to produce a pre-processed heart-related signal 519. The apparatus may comprise a reconstruction unit 516 configured to reconstruct a representation of the heart-related signal to produce a reconstructed representation of the heart-related signal 514, the reconstructing based on a time-varying spectral analysis of the pre-processed heart-related signal 519. The heart-related signal may include motion artifacts, the motion artifacts being signal artifacts produced by movement of the biomedical sensor relative to a sensing location. The pre-processing unit 515 may reduce (i.e., mitigate) the motion artifacts in the pre-processed heart-related signal 519 for the reconstructing. The reconstruction unit 516 may further reduce the motion artifacts reduced by the pre-processing unit 515. The apparatus 520 may further comprise an output unit 518 configured to output the reconstructed representation of the heart-related signal 514.

Pre-processing by the pre-processing unit 515 may include down-sampling the heart-related signal 510 to produce a down-sampled heart-related signal, the down-sampling being at a sampling rate less than an original sampling rate. The time-varying spectral analysis may be based on a frequency resolution and the down-sampling affects the frequency resolution of the time-varying spectral analysis.

The pre-processing unit 515 may be further configured to compute a derivative of the down-sampled heart-related signal to reduce the motion artifacts. The pre-processing unit 515 may be further configured to compute an absolute value of the derivative to further reduce the motion artifacts.

The time-varying spectral analysis may include computing a time-frequency spectrum (TFS) of the pre-processed heart-related signal. The TFS computed may be a 3-dimensional spectra including a time-varying amplitude or power distribution with respect to time and frequency. The TFS computed may be a time-varying power spectral density (PSD).

The reconstruction unit 516 may be further configured to limit the TFS computed to a given frequency range. The given frequency range may be 0.5 Hz to 3 Hz.

The TFS may be computed for each shift of a windowed data segment of the pre-processed heart-related signal 519 and the reconstruction unit 516 may be further configured to reconstruct the heart related signal 510 for each shift of the windowed data segment.

At each shift of the windowed data segment subsequent to an initial windowed data segment, reconstructing the representation may include retaining up to a pre-determined number of frequency spectra to produce a subset of frequency spectra and selecting a frequency component to produce a selected frequency component for the reconstructing. The selected frequency component may be selected from amongst frequency components of the subset of frequency spectra and a previous frequency component, the previous frequency component having been selected for a previous shift of the windowed data segment to reconstruct the heart-related signal for the previous shift.

The time-varying spectral analysis may be a first time-varying spectral analysis and the reconstructing may be further based on a second time-varying spectral analysis of a motion signal 511 (optional), the motion signal 511 (optional) may be output by a motion sensor 509 and representative of the motion artifacts in the heart-related signal 510.

The apparatus 520 may employ the second time-varying spectral analysis of the motion signal to produce a movement classification of the movement. The reconstructing by the reconstruction unit 516 may be further based on the classification of the movement.

The heart-related signal 510 and the motion signal 511 (optional) may be output by the biometric sensor 508 and the motion sensor 509 (optional), concurrently. The apparatus 520 may include the biomedical sensor 508 and the motion sensor 509 (optional). The motion sensor may be an accelerometer. The biomedical sensor 508 may be an electrocardiogram (ECG) sensor.

The apparatus 520 may comprise a heart rate unit (not shown) configured to employ the reconstructed representation 514 to determine a heart rate estimate. The apparatus 520 may comprise a heart rate variability (HRV) unit (not shown) configured to employ the reconstructed representation 514 to determine a heart rate variability (HRV) estimate. The apparatus 520 may comprise an ailment unit (not shown) configured to employ the reconstructed representation 514 to detect or predict a heart-related ailment, the heart-related ailment including at least one of a heart rate variability (HRV) condition, atrial fibrillation condition, congestive heart failure condition, and tachycardia condition.

The reconstruction unit 516, the output unit 518, and the pre-processing unit 515 may be configured to reconstruct, pre-process, and output, respectively, in real-time with respect to outputting of the heart-related signal 510 by the biomedical sensor 508. Alternatively, the reconstruction unit 516, the output unit 518, and the pre-processing unit 515 may be configured to reconstruct, pre-process, and output, respectively, in non-real-time with respect to outputting of the heart-related signal by the biomedical sensor.

The apparatus 520 may be a wearable device, such as a smartwatch, or any other suitable device, such as a wearable personal biometric monitoring device. The apparatus 520 may have a user interface (not shown) to present the reconstructed representation of the heart-related signal 514 or information derived therefrom, such as a characteristic, notification, alarm, or any other suitable information. The reconstructed representation of heart-related signal 514 or the information derived therefrom may be presented to a user via a user interface that may be a visual or audio based user interface.

As disclosed above, according to embodiments disclosed herein, HR and ECG signal reconstruction, may be based on a time-varying spectral analysis. As disclosed above, according to some embodiments, the SegMA method may be comprised of five distinct stages: (1) Taking a derivative of a downsampled ECG (2) obtaining a time-varying power spectral density (PSD) of an absolute value of the derivative, (3) spectral filtering, (4) HR reconstruction, and (5) HRV analysis. If employing a motion signal for the reconstructing, embodiments disclosed herein may employ a window-segmented power spectral density of both ECG and accelerometer signals in real-time to scale each estimate of the PSD by the equivalent noise bandwidth of the window (Stoica, P. and R. L. Moses, Introduction to Spectral Analysis. 1997: Prentice Hall). The simplest way to approach the the time-varying PSD calculation may be to employ the Welch periodogram. However, it has the drawbacks that it is an inconsistent spectrum estimator, has high variance, and has leakage effects (Stoica, P. and R. L. Moses, Introduction to Spectral Analysis. 1997: Prentice Hall). Thus, a dominant spectral peak can lead to an estimated spectrum that contains power in frequency bands where there should be no power. According to embodiments disclosed herein, both problems may be solved by down-sampling the raw signal and taking a derivative of the data and, optionally, an absolute value of the derivative, and then using a sufficiently small frequency step by setting a large number of frequency points. According to some embodiments disclosed herein, a heart-related signal, such as an ECG signal, may be resampled from the original sampling frequency, such as to ¼ of it, and then after taking a derivative of the downsampled signal, and, optionally, an absolute value of the derivative, a periodogram method with frequency resolution of 0.001 may be employed. The PSD spectrum may be limited to a given range, such as a heart rate frequency range of [0.5 Hz-3 Hz], and then the frequency and power information of a predetermined number N of first highest peaks in the PSD, such as a first three highest peaks in the PSD, may be retained at each window and signal segment. Some embodiments disclosed herein may be based on an observation that a heart rate component in a typical clean (motion free) ECG signal is always the dominant frequency component in the time-varying power spectrum, that is, a spectral peak with highest power or amplitude at a time point, and thus, the highest peak of the spectrum corresponds to the HR frequency.

Thus, when movement happens the dominant component can be replaced by movement components which shift the HR to the second peak in the spectrum. A such, embodiments disclosed herein may find two highest peaks and then choose the corresponding frequencies of the ECG to those highest powers in the spectrum. Embodiments disclosed herein may employ a tracking strategy that the highest peak that is closest to the estimated HR of the previous window may be chosen at each window. According to a Results section, disclosed below, the SegMA method not only improves ECG signal and HR reconstruction but also the potential to do heart rate variability analysis on the results. As disclosed below, the SegMA method can improve HR estimations by almost 10 times better accuracy than without SegMA reconstruction.

Experimental Section

An experiment with a physically challenging protocol that includes 17-min ECG recordings from 10 healthy subjects was designed, in which each subject was asked to wear a wrist-worn ECG device as shown in FIG. 1B, disclosed above. Table 5, disclosed below, summarizes various ECG wearable devices including the wrist-worn ECG device. The wearable system is called NohChon and was custom designed in a laboratory. The wearable system comprises two wrist modules which are designed to fabricate a 1-channel ECG signal (Lead I configuration) on the top of right and left wrists. This device was designed and developed for ECG measurement based on two leads with virtual right-leg driven circuit and provides a frequency band at −3 dB from 0.05 to 150 Hz with second-order high-pass and low-pass filters to cover the full ECG range. In both modules, 3-axis accelerometric data were collected to reject MNAs using accelerometer (MMA 8652 FC, Freescale, Tex., USA) which has a sensitivity of ±2 g. A wire was connected between both left and right wrist-based electrodes to produce an ECG signal and is threaded to a compression shirt for minimizing motion artifacts that may be caused by wire movements. The ECG signal was sampled at 360 Hz with 12-bit resolution over a range between 0 and 3.3 volts. Electrodes for ECG measurement are carbon black (CB) based film electrode (Posada-Quintero, H. F., et al., Low Impedance Carbon Adhesive Electrodes with Long Shelf Life. Ann Biomed Eng, 2015. 43 (10): p. 2374-82; Reyes, B. A., et al., Novel electrodes for underwater ECG monitoring. IEEE Trans Biomed Eng, 2014. 61 (6): p. 1863-76).

TABLE 5

ECG Wearable Devices

| Device | Piix (Corventis) [1] | iRhythm (Zio) | Imec ECG necklace [2] | NohChon ECG wrist |
|---|---|---|---|---|
| Sensor modalities | ECG (1-lead), Respiration, Skin Temperature, Body fluids, Accelerometer | ECG (1-lead) | ECG (1-lead), Respiration, Accelerometer | ECG (1-lead), Electrodermal acitivity, Accelerometer |
| Sampling Frequency (ECG) | 200 Hz | 120 Hz | 256 Hz | 360 Hz |
| Analog front-end | Not disclosed | Not disclosed | imec ULP 1-ch ECG ASIC | Instrumentation amplifier |
| ADC resolution | 10-bits | 10-bits | 12-bits | 12-bits |
| Functionality | Event detection (Arrhythmia) | None | Beat-to-beat HR and HRV, seizure detection | Motion Artifact Reduction, Beat-to-beat HR and HRV |
| Wireless Connectivity | Event sent to z-link; and downloaded for off-line analysis | None | Real-time interface to mobile phone (using dongle) | Real-time interface to smart devices (using Bluetooth) |
| Power consumption | 40 mW | Not disclosed | 3 mW (data streaming); 7 mW (embedded data processing) | 100 mW (data processing and transmitting via Bluetooth) |
| Form factor | Patch (160 mm × 60 mm) | Patch (123 mm × 53 mm) | Necklace (60 mm × 40 mm) + lead wires to disposable electrodes | Wrist bands + CB film electrodes (2.5 mm × 2.5 mm) |
| Usability | Disposable | Recycle | Disposable | Disposable |

The electrode is comprised of adhesive so it enables collection of stable ECG signal even without hydrogel, and there was no complaint about skin irritation from the subjects. Each subject was asked to perform different types of physical activities (see Table 6) during the experiment to investigate the performance of the SegMA method in variety types of daily activities and movements. The reference ECG signals for evaluation of SegMA were recorded from a chest using Holter monitor. Table 5, disclosed above, presents various ECG wearable patches and devices in comparison to the NohChon wearable module.

TABLE 6

ECG Datasets and Experiments Settings

| [3]Subject | Dataset | Activity Type | Setup | Subject's Age/Sex |
|---|---|---|---|---|
| 1 | 3 (Chon Lab) | Depicted in Table (2) | See FIG. 1B | 26-55 y (10 Males) |
| 2 | | | | |
| 3 | | | | |
| 4 | | | | |
| 5 | | | | |
| 6 | | | | |
| 7 | | | | |
| 8 | | | | |
| 9 | | | | |
| 10 | | | | |

Table 7, disclosed below, represents the experimental protocol of ECG data collection. A video of the activities each subject performed during the experiment is available from (Laughlin, M. H., Cardiovascular response to exercise. Am J Physiol, 1999. 277 (6 Pt 2): p. S244-59).

TABLE 7

Experiment Protocol

| | | Activity Type | | | | | | |
|---|---|---|---|---|---|---|---|---|
| | Rest (Supine Position) | Walking (2 mph) Jogging (4 mph) Running (6 mph) | Rest (Standing) | Standing/Sitting on a arm chair | Arm Movements (Up/Down) and (Left/Right) | Wrist Rotation/Shaking | Weight Lifting and Box Moving | Deep Breathing |
| Duration (min) | 5 | 1.5 | 0.5 | 0.5 | 3 | 3 | 3 | 0.5 |

Methodology

Embodiments of the SegMA method employed for the HR monitoring during intensive movements are summarized in Table 1, disclosed above. Details of each stage are disclosed in subsections i to v, below.

i. ECG Pre-processing

The first phase of the SegMA method may be to resample the ECG signal to ¼ (that is, downsample) of its original sampling rate. This improves the frequency resolution in the time-frequency spectrum. Next a derivative of the resampled ECG signal may be computed so that the R-peaks are accentuated. The idea is that motion and noise artifacts can be reduced to some extent via the derivative as long as the motion is not abrupt and the samples are uniformly corrupted by motion. Further, optionally, an absolute value of the derivative may be taken to further accentuate the R-peaks.

Figure 6A:
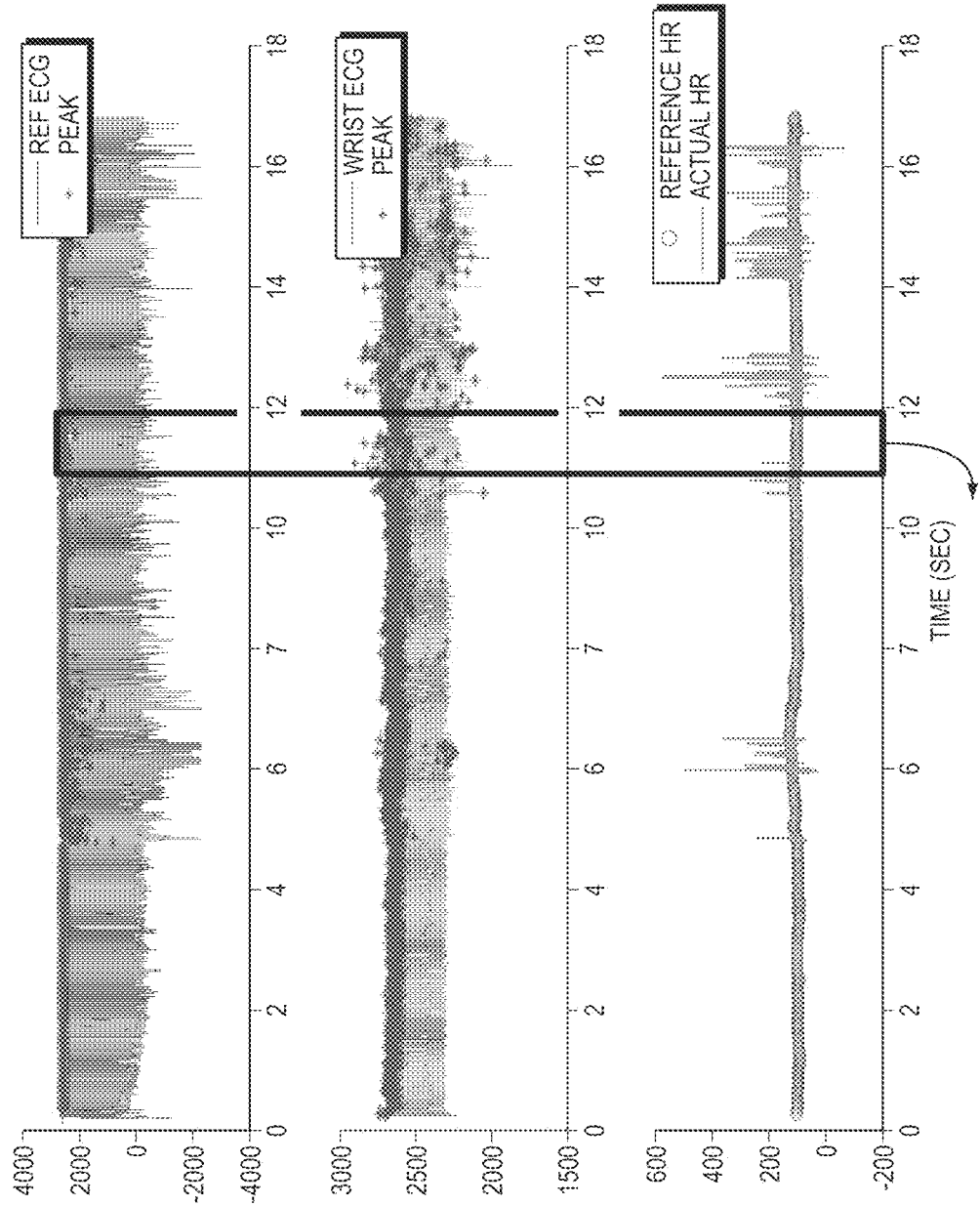
FIG. 6A is a plot of ECG recordings and estimated heart rate (HR).
Figure 6B:
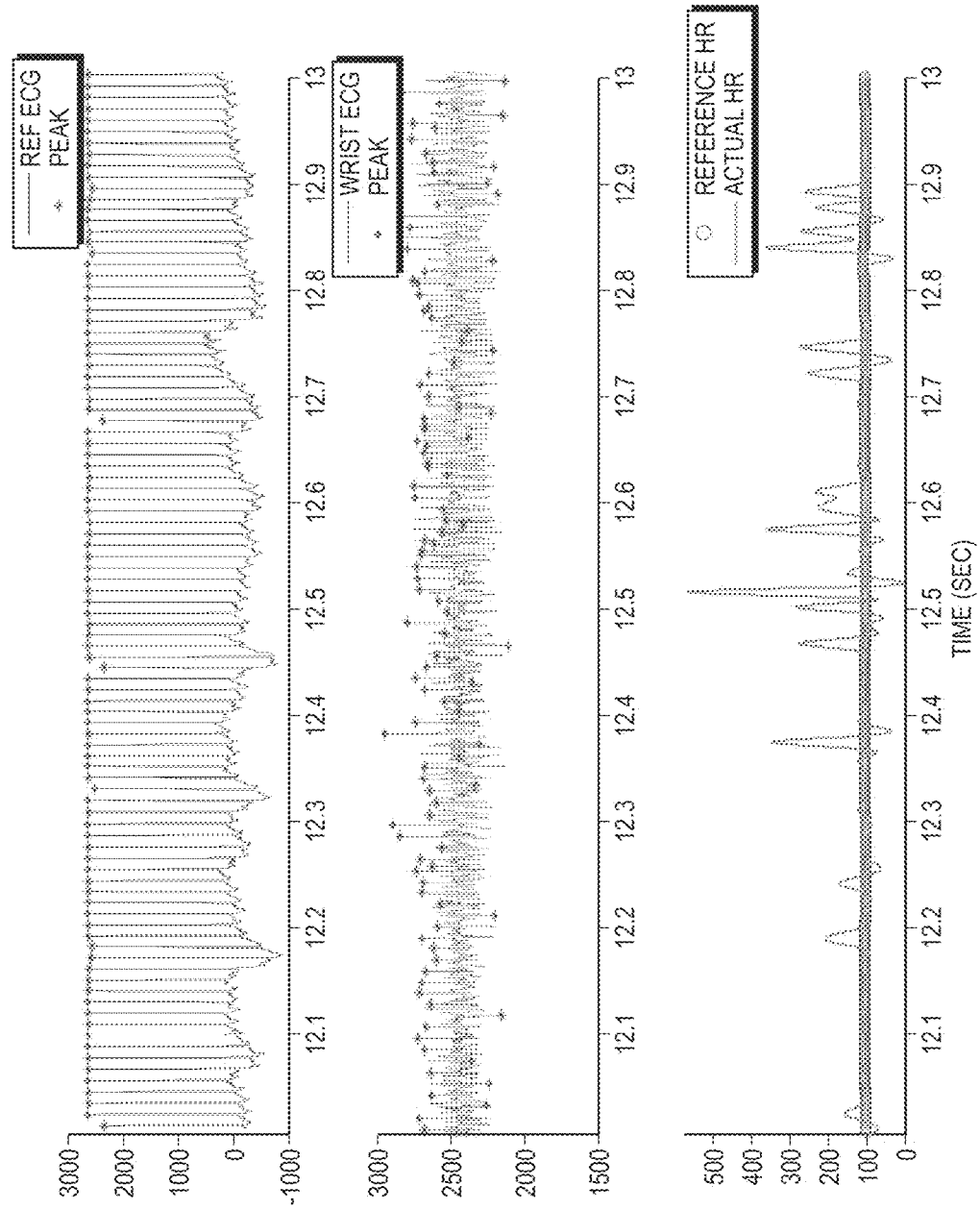
FIG. 6B is a zoomed in version of FIG. 6A.

FIGS. 6A-B show representative ECG recordings from both the NohChon wrist device (Wrist ECG) and the Holter (Ref ECG). Specifically, FIG. 6A is a plot of ECG recordings and estimated HR from subject #3; [top]: reference ECG, [middle]: Wrist ECG, and [bottom] reference HR vs actual HR.

FIG. 6B is a zoomed in version of FIG. 6A. FIGS. 6A-B show the HR estimations from R-R intervals of the reference HR and the wrist ECG. The reference HR provides a clean and accurate HR and the estimated HR from the wrist ECG signifies inaccurate HR estimation especially during running, wrist movements, and weight lifting periods of experiment. FIGS. 6A-B indicate a reason for using a HR reconstruction approach according to embodiments disclosed herein.

ii. Time-Varying Spectral Analysis of ECG Data

Embodiments disclosed herein may obtain a time-varying spectrum by taking a T-sec window of the ECG signal and computing a power spectral density (PSD) of the segment and then sliding the window through the whole dataset which yields a time-frequency matrix in which each array represents the power of the signal corresponding to a specific frequency and sliding time-step (shift) of S-sec. The sliding process and frequency step specify the resolution and dimension of the time-frequency matrix.

Embodiments disclosed herein may employ two different sliding window approaches depending on the application. For estimating either heart rates or heart rate variability, data may be shifted sample-by-sample with no overlap for the entire dataset. Such a sliding window approach enables capturing beat-to-beat dynamics of HRV which requires sample-to-sample estimation of PSD. Given a downsampled data of Fs=20 Hz, each data point may be shifted by 0.05 seconds. For estimating only the heart rates, the data may be shifted segment-by-segment rather than sample-by-sample. Such a coarse-grain windowing approach has less computational cost and it can provide good tracking of heart rates, but may not be useful for HRV. For the experimental results, a window segment length T was set to 8 seconds and was shifted (S) by 2 seconds. The 8 second data segment and the shift of 2 seconds were chosen because one of the goals was to compare the SegMA method results to other methods which have used this chosen data segment length and time shift. Moreover, the assumption of an 8 second data length largely stems from the fact that heart rates do not change instantaneously, hence, an 8 second duration may be a reasonable choice. Hence, according to embodiments disclosed herein, a time-frequency spectrum of the derivative of the resampled ECG may be computed.

Figure 7A:
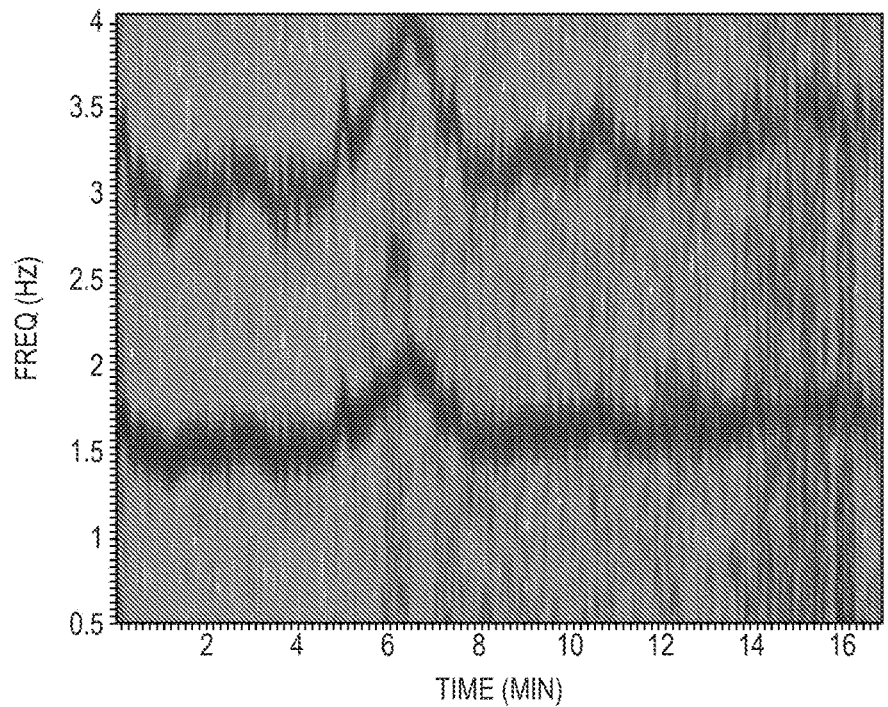
FIG. 7A is a plot of an ECG time-frequency spectrum.

FIG. 7A is a plot of an ECG time-frequency spectrum. As a representative example, the resultant frequency components in the time-frequency matrix of recordings from subject #3 of the dataset, for a window length of 8 seconds that is shifted by every 2 seconds, is shown in FIG. 7A.

Figure 7B:
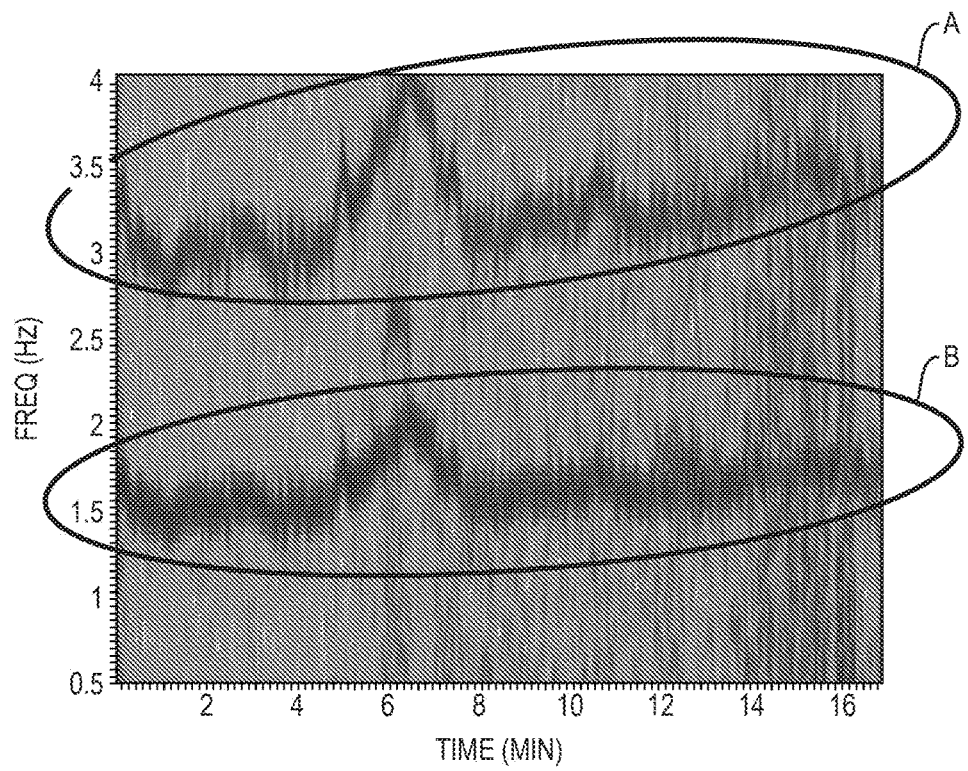
FIG. 7B is an annotated plot of the ECG time-frequency spectrum of FIG. 7A.

FIG. 7B is a plot of the example ECG time-frequency spectrum from FIG. 7A. In FIG. 7B, two major frequency components (A) and (B) are observed in the time-frequency spectrum plot: one of them appears to represent HR and the other may represent the first harmonic of HR. In order to verify this conjecture these components may be extracted from the time-frequency spectrum. To this end, in another phase of the SegMA method, Spectral Filtering, disclosed below, a filtering strategy may be applied to keep (i.e., preserve, retain) the major components of the spectrum and remove the unnecessary information.

iii. Spectral Filtering

Based on an assumption that the HR frequency component is the dominant peak in the power spectral density (PSD) of each 8 sec window of a clean ECG signal, the filtered time-frequency spectrum using the first two largest peaks of PSD at each window can be extracted, as shown in FIG. 8A, disclosed below.

FIG. 8A is a plot of a time-frequency spectrum: Blue, Green circles correspond to the first two highest peaks in the defined HR frequency range of (30-180 bpm), respectively, at each sliding window. FIG. 8B is a plot showing tracking of the HR trace in the filtered ECG spectrum of FIG. 8A.

From the time-frequency spectrum of FIG. 8A, the first two largest peaks of PSD at each window can be extracted, according to embodiments disclosed herein. After obtaining the power spectral density at each window, the HR frequency is assumed to be confined in the range [0.5 Hz-3 Hz], which takes into account both at rest and high HR due to either tachycardia or exercise scenarios. Hence, for HR estimation, the strategy is to eliminate frequencies that are outside of this HR frequency range as they are most likely due to motion artifacts or harmonics of the HR frequency.

In general, HR frequency in the power spectral density of ECG at each window can have three different scenarios: (1) ECG is devoid of MA and there is no spatial gap between the electrode and the subject's skin during recording, (2) ECG is corrupted by MA and there is no spatial gap between the electrode and the subject's skin during recording, and (3) There is a spatial gap between the electrode and the subject's skin during recording. For the ideal case (1), HR can be extracted and it is most likely represented as the highest peak in the ECG spectrum. For case (2), MA dynamics can result in the dominant peak and HR frequency peak's magnitude become smaller than the MA frequency peak in the power spectrum. The only scenario that makes it difficult to extract HR from the spectrum is scenario (3) when there is a spatial gap between the ECG electrodes and the subject's skin during recording. In this scenario, assuming that the motion artifacts are short lasting, the missing HR values can be interpolated using the cubic spline approach. Turning back to FIG. 8A, FIG. 8A shows retaining only the two largest frequency peaks at each time point within the defined HR range (30-180 bpm) and they are represented as blue and green colors, respectively. Retaining only the two largest frequency peaks at each time point may be reasonable for the first two cases, outlined above. The component (A) is distinguishable from the filtered spectrum, as shown in FIG. 8A.

iv. Heart Rate Tracking & Extraction

According to embodiments disclosed herein, a next phase may be to extract HR frequencies with time, such as the frequency components of FIG. 8A, disclosed above. Note that in FIG. 8A, there are two peaks at each time instance, thus, the question is how to identify which of the two peaks represents the HR at each time point. For the initial time window of 8 seconds, a clean data segment may be employed, so that true HR can be determined. This scenario is case 1 described above in the spectral filtering section, and the detection of HR may simply be the highest peak in the spectrum. Next, HR may be estimated for each sliding window of data and a HR peak may be chosen (i.e., selected, extracted) from the ECG spectrum with the knowledge of estimated HR values in previous time windows.

Two main scenarios may be considered: (1) no peak exists in the spectrum that can represent HR, and (2) there is a spectral peak among the first two highest peaks of spectrum that belongs to the HR component. In case (1), where HR is not detectable in the window (e.g., due to spatial gap between the ECG electrode and skin), a real-time implementation of the SegMA method may take the previous window's HR value as the current HR (or simply use the moving average of several past HR beats or some other variant). In offline processing (i.e., non-real time), a cubic spline interpolation can be used to fill in the missing HR information. In the more general case (2), where the HR peak is among the first two highest peaks in the spectrum, two possible scenarios can occur: (2-A) the windowed ECG signal is clean and the first highest peak in the spectrum represents the HR fundamental frequency, (2-B) the windowed ECG signal is corrupted by movement and the second peak corresponds to HR, (2-C) while the HR spectral peak is detectable, the difference between its value and that of the previous HR may be more than a given difference value (also referred to interchangeably herein as a given distance value), such as 10 bpm (beats-per-minute) or 15 bpm, or any other suitable difference value, so it may be replaced by the most recent HR value from a previous window segment (or a moving average of several past HR beats or some other variant). According to some embodiments, a criterion may be set that the HR value cannot change more than the given difference value, such as 15 bpm, from a previous time window. It can be observed from FIG. 8B, disclosed above, that in most cases, the blue circle which represents the largest spectral peak is chosen but in other cases, green circles are chosen for certain time points. For the HR peaks associated with the green circles, they are chosen because either the first highest peak is related to a motion artifact or the highest magnitude peak deviates more than the given difference value, such as 15 bpm, from the previous HR value.

Figure 9:
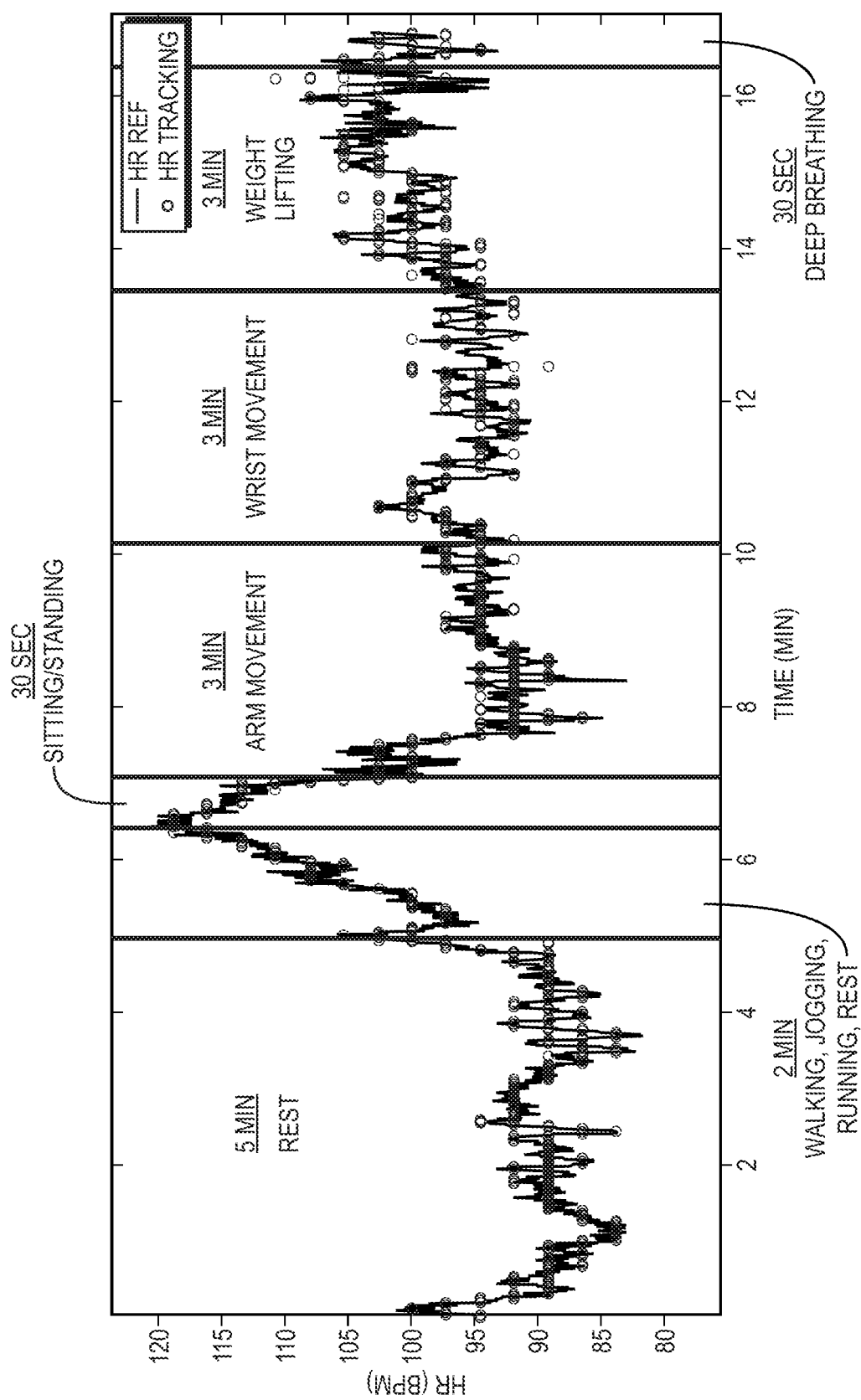
FIG. 9 is a plot showing tracking of reconstructed HR compared to a reference HR.

FIG. 9 is a plot showing the tracking of reconstructed HR compared to the reference during different activities involved in the experiment. FIG. 9. shows a comparison of reference HR to the HR tracking from filtered time-frequency spectrum of ECG recordings from subject #3, labeled with respective type of activities.

Figure 10:
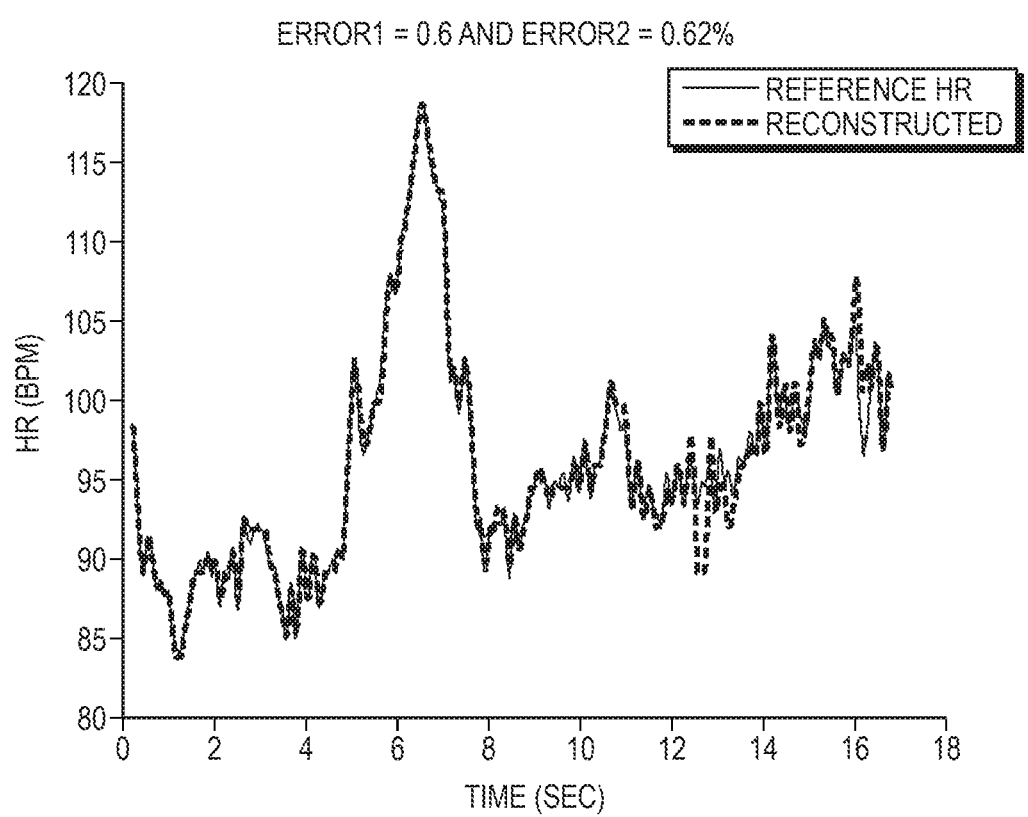
FIG. 10 shows a comparison between a reconstructed HR and a reference HR.

FIG. 10 shows a comparison of reconstructed HR obtained from SegMA, estimated from simultaneous ECG recordings#3, to a reference HR. FIG. 10 shows the SegMA reconstructed HR (red color) from ECG spectra of recording#3 using SegMA along with the 8-sec moving average of reference ECG-derived HR (black color). In order to calculate the performance of the SegMA method, the error value in each time window was calculated from the estimated HR to the reference ECG-derived HR.

Two measurement indices of absolute error similar to the indices in (Rahman, M. Z. U., R. A. Shaik, and D. V. R. K. Reddy. An Efficient Noise Cancellation Technique to Remove Noise from the ECG Signal Using Normalized Signed Regressor LMS Algorithm. in Bioinformatics and Biomedicine, 2009. BIBM '09. IEEE International Conference on. 2009) were used.

$$\text{Error}(1) = \frac{1}{W}\sum_{k=1}^{w} |HR_{SegMA}(k) - HR_{ref}(k)| \quad (1)$$

$$\text{Error}(2) = \frac{1}{W}\sum_{k=1}^{w} \frac{|HR_{SegMA}(k) - HR_{ref}(k)|}{HR_{ref}(k)} \times 100\% \quad (2)$$

v. Heart Rate Variability analysis

For an HRV analysis application, the above-disclosed procedures are identical but the only difference is a beat-by-beat shift of data rather than the 8 second data segment shift or it's variant.

Figure 11A:
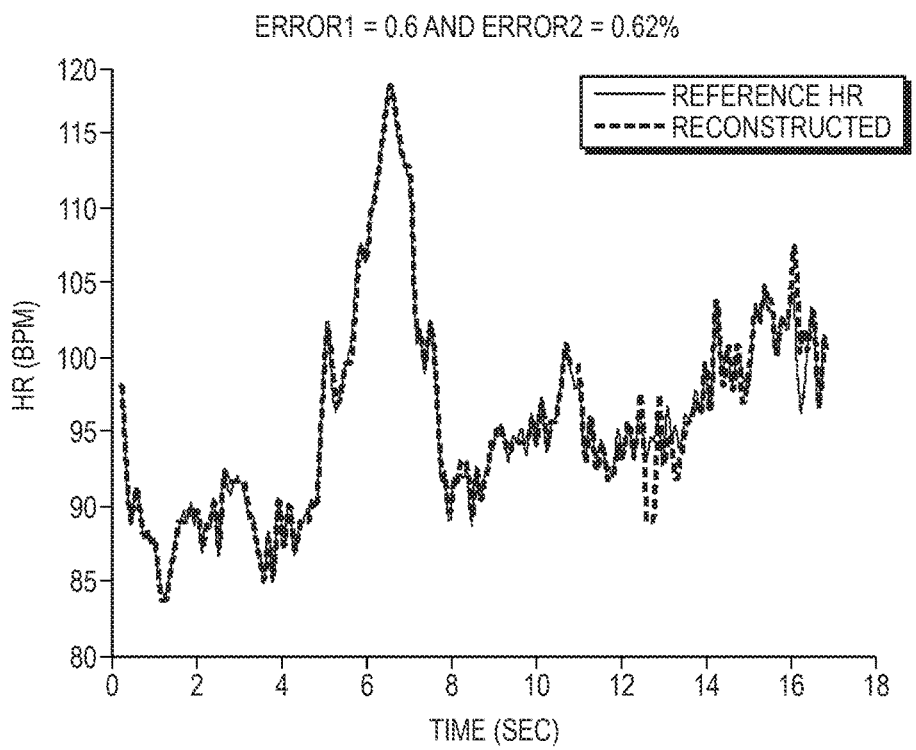
FIG. 11A shows a beat-by-beat reconstruction of HR.

FIG. 11A shows a beat-by-beat reconstruction of HR using SegMA. FIG. 11A shows a time-domain comparison of reconstructed and reference HR.

Figure 11B:
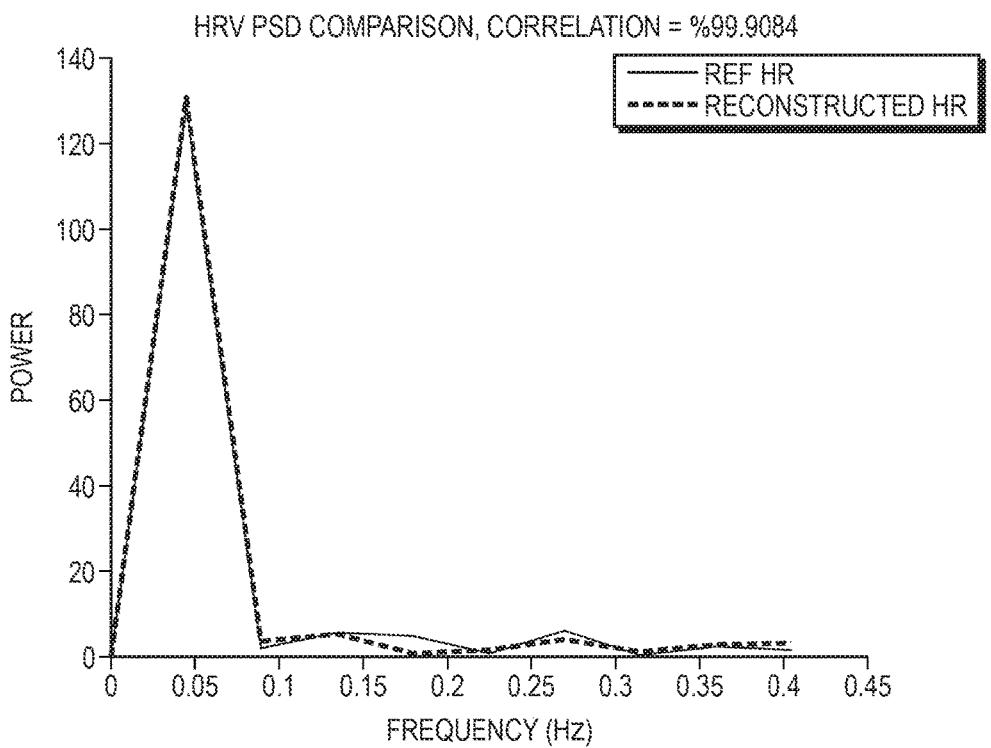
FIG. 11B shows a power spectral density of reconstructed HR.

FIG. 11B shows the power spectral density of reconstructed HR. It can be observed that the correlation between PSD of estimated SegMA and reference HRV in the frequency range of [0-0.4] Hz is almost 100%. The spectral comparison of heart rate variability between the reconstructed HR and reference HR was calculated from the reference ECG using Pan & Tompkin peak detection approach (F. Yazicioglu, T. T., J. Penders, I. Romero, H. Kim, P. Merken, B. Gyselinckx, H. J. Yoo, C. Van Hoof. Ultra-low-power wireless sensor nodes. in Proceedings of the 31st Annual International Conference of the IEEE EMBS. 2009. Minneapolis: IEEE).

Results

Table 8, disclosed below, represents the average absolute error (E1) and the average absolute error percentage (E2) of HR estimations of the SegMA method on the dataset. The SegMA method is compared to the HR estimations before applying the reconstruction method, where both before and after reconstruction estimations are compared to the reference HR from ECG, and reference SpO2 from a Masimo commercial device. The forth column in Table 8 shows that SegMA on average improves the HR estimations with almost 1000% comparing to those estimations before reconstruction. The improvement rate was calculated as follows:

$$\text{ImRate1}(\%) = \frac{1}{W}\sum_{k=1}^{w} \frac{|\text{Error1}_{SegMA}(k) - \text{Error1}_{Act}(k)|}{\text{Error1}_{SegMA}(k)} \times 100\% \quad (3)$$

$$\text{ImRate2}(\%) = \frac{1}{W}\sum_{k=1}^{w} \frac{|\text{Error2}_{SegMA}(k) - \text{Error2}_{Act}(k)|}{\text{Error2}_{SegMA}(k)} \times 100\% \quad (4)$$

TABLE 8

SegMA Method Performance Comparison

| | Actual HR estimation error | | SegMA HR estimation error | | SegMA Improvement Rate | |
|---|---|---|---|---|---|---|
| Subject | E1 | E2% | E1 | E2% | ImRate 1% | ImRate 1% |
| 1 | 13.66 | 13.98 | 1.31 | 1.46 | 943.1 | 857.5 |
| 2 | 22.69 | 24.37 | 2.05 | 2.16 | 1006.9 | 1028.2 |
| 3 | 8.66 | 8.71 | 0.60 | 0.62 | 1343.3 | 1304.8 |
| 4 | 15.32 | 15.06 | 1.64 | 1.78 | 834.4 | 746.1 |
| 5 | 33.32 | 31.87 | 4.87 | 5.50 | 584.20 | 479.4 |
| 6 | 20.84 | 21.56 | 2.43 | 2.61 | 757.66 | 726.05 |
| 7 | 26.85 | 23.93 | 2.61 | 2.31 | 928.7 | 935.9 |

TABLE 8-continued

SegMA Method Performance Comparison

| Subject | Actual HR estimation error | | SegMA HR estimation error | | SegMA Improvement Rate | |
|---|---|---|---|---|---|---|
| | E1 | E2% | E1 | E2% | ImRate 1% | ImRate 1% |
| 8 | 16.15 | 16.66 | 0.97 | 1.00 | 1582.3 | 1582.8 |
| 9 | 10.19 | 10.83 | 0.72 | 0.75 | 1315.7 | 1344.2 |
| 10 | 9.43 | 9.37 | 0.84 | 0.93 | 1022.6 | 907.5 |
| mean ± std | 17.71 ± 8.1 | 17.63 ± 7.6 | 1.80 ± 1.3 | 1.91 ± 1.4 | 1031.9 ± 300.8 | 991.2 ± 332.4 |

FIGS. 12A-B, 13A-B, and 14A-B show the reconstructed HR and corresponding PSD of a sample-sample windowed HR in comparison to the reference HR from an ECG.

Figure 12A:
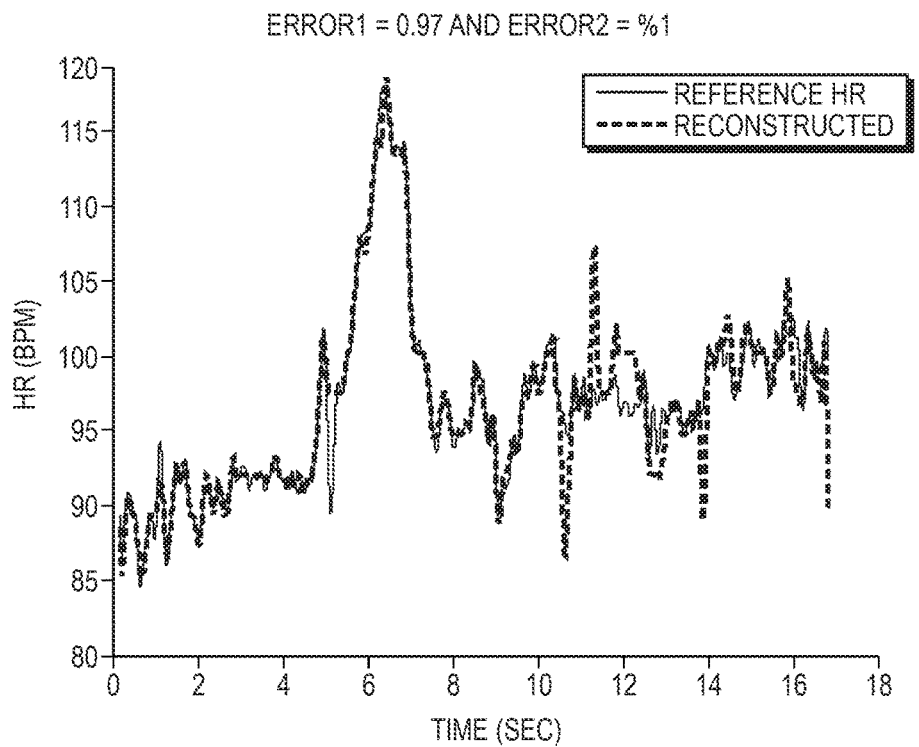
FIGS. 12A-B, 13A-B, and 14A-B show reconstructed HR and corresponding power spectral density (PSD) in comparison to a reference HR from an ECG.

FIG. 12A shows the Reconstructed HR vs. reference HR for subject #8.

Figure 12B:
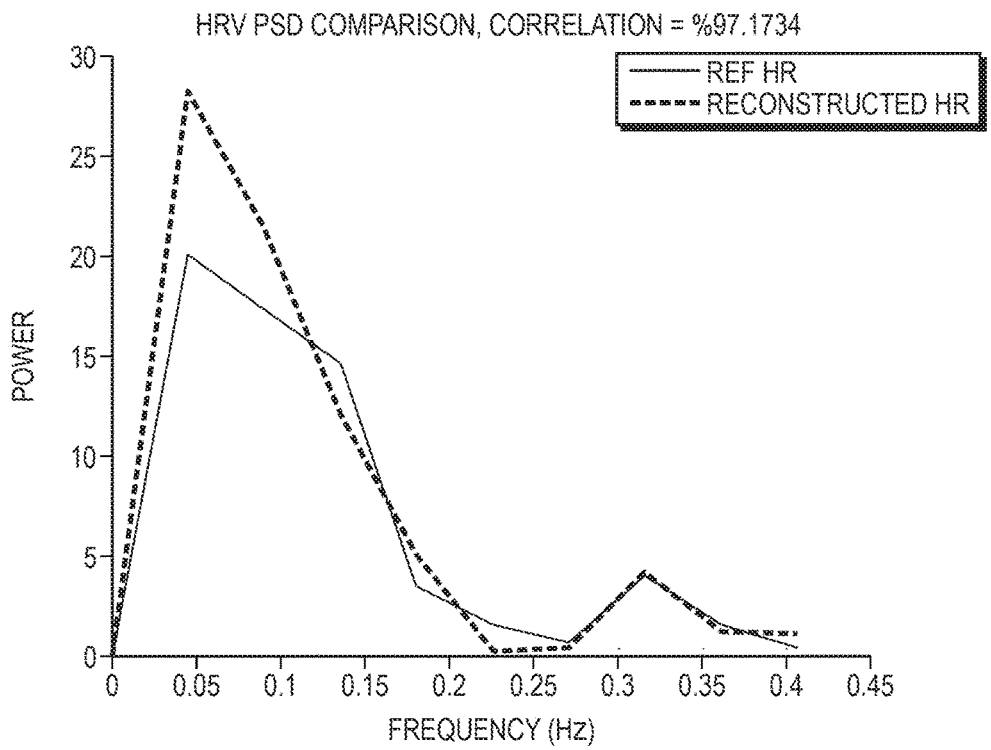

FIG. 12B shows a spectral comparison of reconstructed HR and reference HR (estimated from reference ECG). As can be observed, the E1 for this particular subject is as low as 0.97 bpm and the correlation between the PSD of reconstructed HR and reference HR is as high as 97%.

Figure 13A:
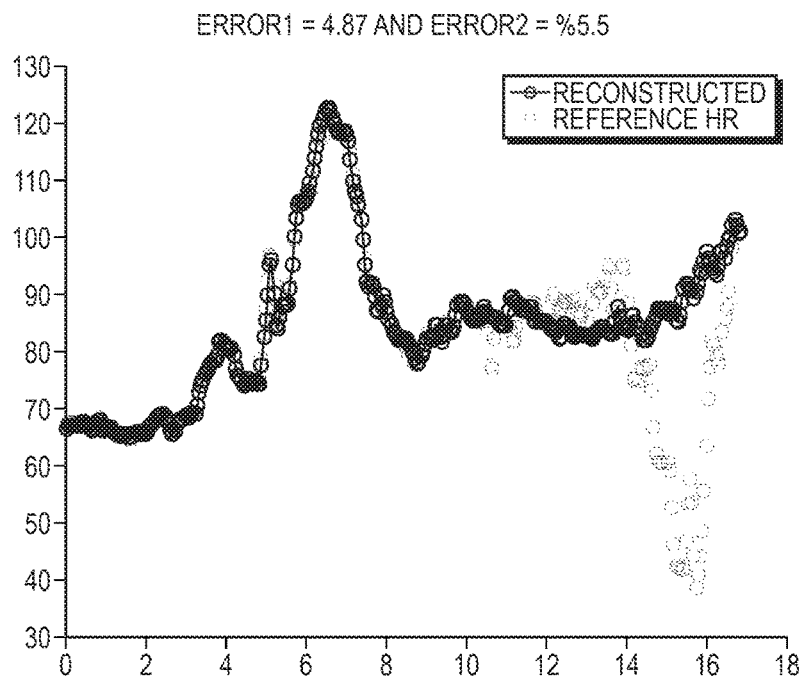

FIG. 13A shows the Reconstructed HR vs. reference HR for subject #5. FIG. 13A shows the comparison between the reconstructed HR and the reference HR for subject #5 and recording #7 that have the highest errors. Higher error from recording #7 can be due to rapid changes of physiological HR and the motion artifacts during the activities. In the case of subject #5, it can be observed that the error is due to losing track of HR during weight lifting activity. This could be due to skin-electrode interface gap.

Figure 13B:
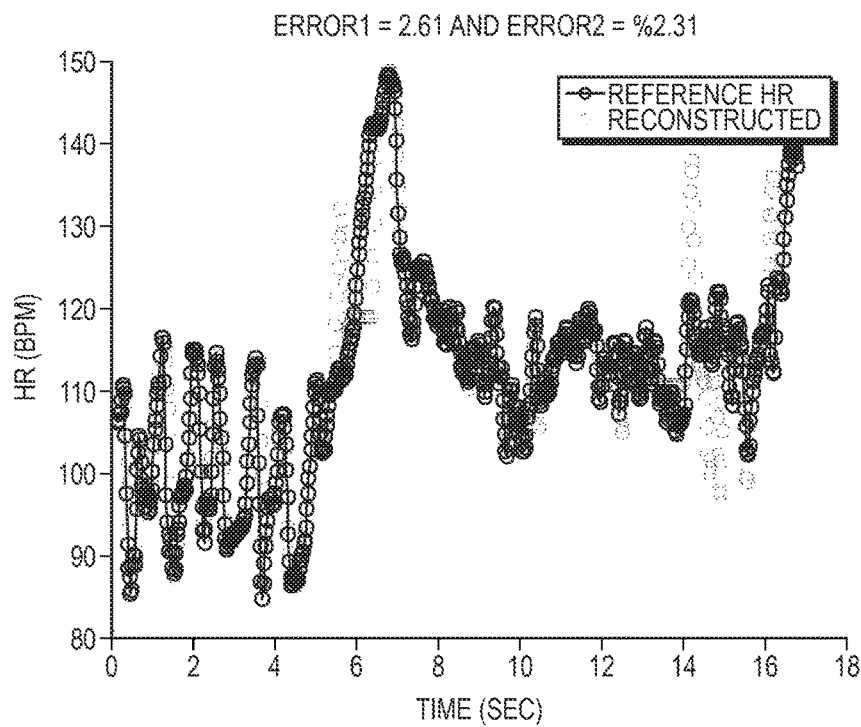

FIG. 13B shows the Reconstructed HR vs. reference HR for subject #7.

Figure 14A:
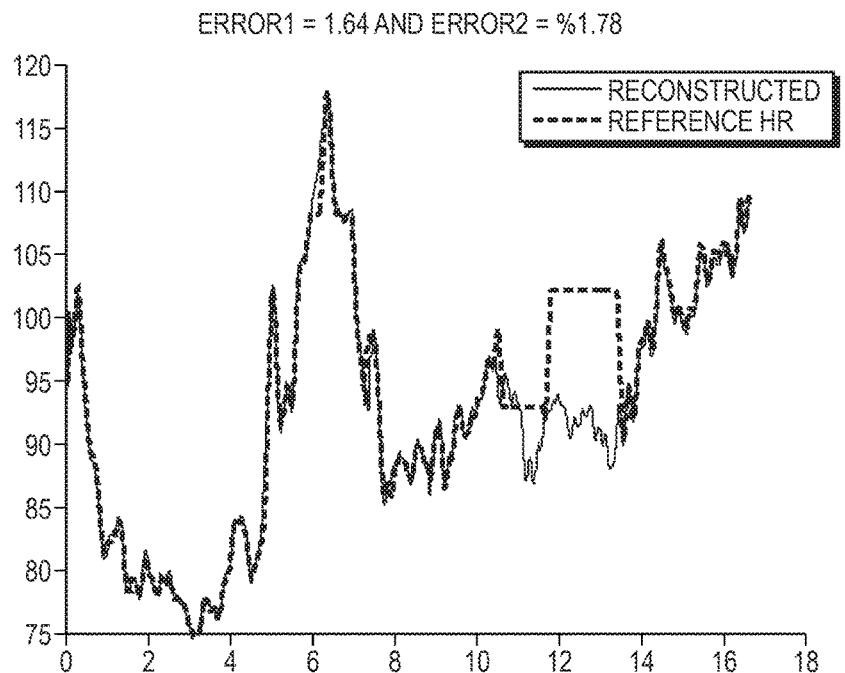

FIG. 14A shows the Reconstructed HR vs. reference HR for subject #4.

Figure 14B:
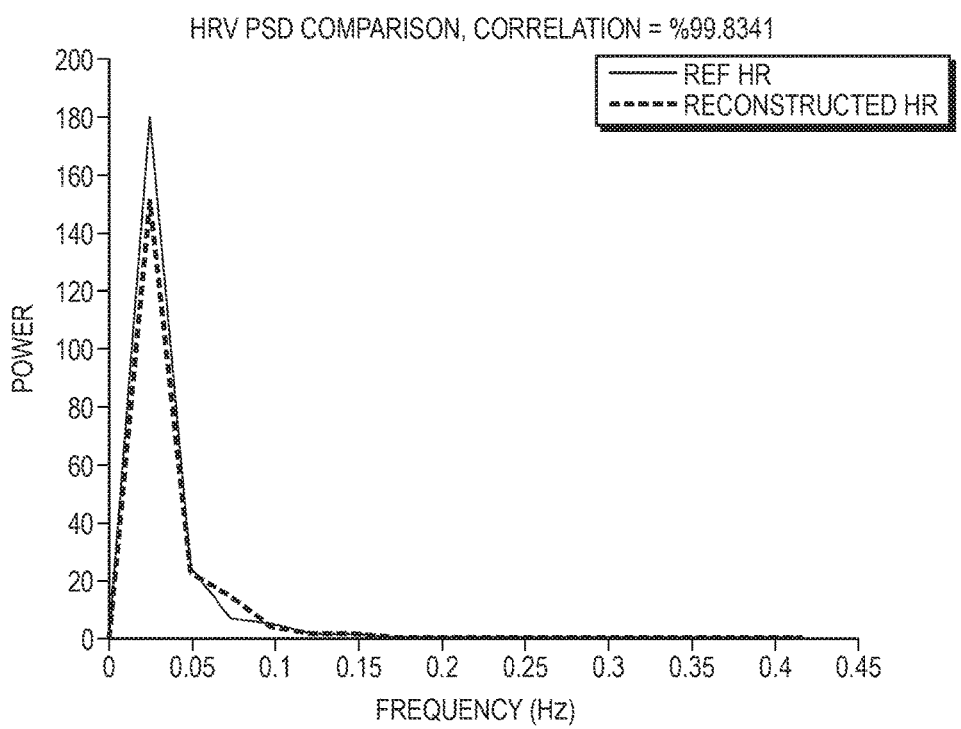

FIG. 14B shows a spectral comparison of reconstructed HR and reference HR (estimated from reference ECG). It can be seen that the E1 for this subject is around 1.7 bpm and the correlation between the PSD of reconstructed HR and reference HR is as high as 99%.

All subjects' results are provided in Table 10. Table 10 represents the correlation and statistical difference using the student's t-test between PSD of estimated and reference HRV in both LF (0.04-0.15 Hz) and HF (0.15-0.4 Hz) frequency ranges. The correlation values in the table are calculated based on Pearson's linear correlation coefficient. As shown in Table 9, there was no difference between the reference and SegMA-derived HRV for LF in all but one subject and the difference was seen in only 4 out of 10 subjects for HF. Table 10 shows some of the widely-reported time-domain HRV parameters such as the mean HR, standard-deviation (SDNN) of the normal-to-normal (NN) interval, root-mean-square of successive difference (RMSSD) of the NN interval, and the number of interval differences of successive NN intervals greater than 50 ms divided by the total number of NN intervals (pNN50) estimated from SpaMA in comparison to the reference ECG NN interval. None of these parameters were found to be significantly different between the SegMA-derived and the reference HRV.

TABLE 9

Frequency Domain HRV analysis Comparison: PSD of SpaMA vs. reference

| | Correlation | |
|---|---|---|
| Subjects | LF (LF is [0.04-0.15] Hz and HF is [0.15-0.4] Hz) | HF |
| 1 | 0.99 | 0.98 |
| 2 | 0.98 | 0.95* |
| 3 | 1.00 | 0.98 |
| 4 | 1.00 | 0.99 |
| 5 | 0.94* | 0.85* |
| | (Statistical difference) | |
| 6 | 0.97 | 0.91* |
| 7 | 0.96 | 0.90* |
| 8 | 0.97 | 0.98 |
| 9 | 1.00 | 0.99 |
| 10 | 1.00 | 0.99 |
| mean | 0.99 | 0.96 |

TABLE 10

Time Domain HRV analysis Comparison: SpaMA vs. reference HRV

| | SDNN | | meanNN | | RMSSD | | pNN50 | |
|---|---|---|---|---|---|---|---|---|
| Subjects | SpaMA | Reference | SpaMA | Reference | SpaMA | Reference | SpaMA | Reference |
| 1 | 1874.70 | 1729.15 | 28097.82 | 28087.09 | 18.15 | 14.10 | 0.044 | 0.007 |
| 2 | 1996.62 | 1998.02 | 28157.83 | 28231.82 | 31.09 | 15.43 | 0.019 | 0.011 |
| 3 | 2987.54 | 3005.81 | 24278.31 | 24517.17 | 44.90 | 36.69 | 0.112 | 0.125 |
| 4 | 2129.40 | 1993.10 | 10313.61 | 11764.64 | 22.64 | 18.12 | 0.016 | 0.016 |
| 5 | 1493.53 | 1529.24 | 14591.50 | 13100.12 | 43.50 | 74.97 | 0.039 | 0.046 |
| 6 | 2153.20 | 2246.96 | 14357.50 | 14398.22 | 45.81 | 69.78 | 0.022 | 0.022 |
| 7 | 1980.40 | 1993.71 | 12181.57 | 11762.11 | 28.28 | 18.11 | 0.015 | 0.016 |
| 8 | 6757.14 | 6405.54 | 15858.31 | 16916.03 | 60.75 | 98.69 | 0.031 | 0.292 |
| 9 | 2544.54 | 2693.81 | 14778.82 | 13940.62 | 39.58 | 44.95 | 0.013 | 0.012 |
| 10 | 3481.65 | 3502.19 | 11525.21 | 12091.71 | 36.77 | 53.45 | 0.041 | 0.017 |
| p-value | >0.05 | | >0.05 | | >0.05 | | >0.05 | |

A video of the real-time implementation of SegMA is available from (Laughlin, M. H., Cardiovascular response to exercise. Am J Physiol, 1999. 277 (6 Pt 2): p. S244-59).

Discussion and Conclusions

Wearable sensors have recently enjoyed much public attention and interests. This is well deserved as many wrist-worn devices promise to provide reasonable estimates of heart rates and other health related information including the calories burned based on the number of steps or activities taken throughout the course of a day. More importantly, these devices provide an attractive feature where for the first time individuals can track and manage their own health-related data. In spirit of these recent development in wrist-worn sensors, the objective of embodiments disclosed herein was to develop a robust and accurate method that can mitigate motion artifacts so that more accurate heart rates and other relevant diagnostic information can be estimated. Certainly, this is challenging since wrist-worn devices are especially prone to more challenging and varied motion artifacts when compared to sensors placed on other parts of the body.

While wearable ECG devices are normally worn as either a Holter monitor or a patch on the chest, recent advances in non-contact capacitive and dry electrodes has resulted in textile worn ECG measurements. The form factor and locations of these textile-based ECG sensors can be found from the traditional ECG electrode placements around the chest area to electrodes incorporated directly into a belt (Posada-Quintero, H. F., et al., Low Impedance Carbon Adhesive Electrodes with Long Shelf Life. Ann Biomed Eng, 2015. 43 (10): p. 2374-82, and Reyes, B. A., et al., Novel electrodes for underwater ECG monitoring. IEEE Trans Biomed Eng, 2014. 61 (6): p. 1863-76.

A custom wrist-worn ECG device using custom dry flexible electrodes (Posada-Quintero, H. F., et al., Low Impedance Carbon Adhesive Electrodes with Long Shelf Life. Ann Biomed Eng, 2015. 43 (10): p. 2374-82; Reyes, B. A., et al., Novel electrodes for underwater ECG monitoring. IEEE Trans Biomed Eng, 2014. 61 (6): p. 1863-76) was developed and this is the device that was used to collect experimental data as disclosed above.

As disclosed above, SegMA, based on time-varying spectral analysis of the ECG signal is introduced to combat (i.e., suppress, reduce, mitigate) motion artifacts. To fully test the robustness of the SegMA method, a design for the types of motion artifacts introduced for the experiments was cognizant of the wide variety movements subjects might encounter during their daily activities. In all of the recordings, the reference HR was calculated from an ECG signal that was collected simultaneously with the ECG signal. The estimated HR was calculated from the spectrum of ECG in 8 second time windows. It was shown that the SegMA method can be used for tracking fast HR changes as they varied more than 70 beats/min in less than 2 minutes and despite severe motion artifacts since the subjects were running at a full speed on a treadmill, the average error of just 1.80 bpm was found when compared to that of the reference ECG. This average error also includes when subjects were introducing challenging motion artifacts by performing wrist shaking and bending exercises.

The results from Table 8, disclosed above, show that the SegMA method can be effectively applied to monitor HR from ECG wrist wearable devices. Several observations were made while analyzing the data. The tracking ability of the SegMA method decreased as the dynamics of the motion artifact increased. This phenomenon mostly was observed while dealing with the subject #7 and is due to fast changing HR and abrupt movements which consequently made it more difficult to track the HR-related frequencies in the spectrum.

The main sources of noise and corruption during recording ECG signal using NohChon wrist band was (1) movement of wire inside of tight suit, (2) electromyogram (EMG) interference when subjects were either shaking or bending the wrist, and (3) contact issues with the skin-electrode interface during movements. SegMA has been shown to address the first two type of noise and motion artifacts. However the third noise type which can be due to gaps or poor contact between skin-electrode interfaces is the most challenging scenario for any motion artifact reconstruction method. This is because a gap between electrode and skin, ECG signal strength would decrease due to impedance mismatch (Taji, B., et al., Impact of Skin–Electrode Interface on Electrocardiogram Measurements Using Conductive Textile Electrodes. Instrumentation and Measurement, IEEE Transactions on, 2014. 63 (6): p. 1412-1422), and if severe, it can lead to loss of signal. The electrodes used in for the experiments were a thin flexible film type made out of carbon black powder adhered to a skin with adhesive (Posada-Quintero, H. F., et al., Low Impedance Carbon Adhesive Electrodes with Long Shelf Life. Ann Biomed Eng, 2015. 43 (10): p. 2374-82; Reyes, B. A., et al., Novel electrodes for underwater ECG monitoring. IEEE Trans Biomed Eng, 2014. 61 (6): p. 1863-76), but it can wrinkle or loose contact with the skin when subjected to severe bending or flexing motions. Certainly, this type of noise could be minimized by choosing electrodes that have thicker foam electrodes that cannot be deformed easily. However, the tradeoff is that certain flexible exercises are possible with these thicker electrodes as they may all together pop off the skin depending on the severity of the flexing exercises. Among the 10 recordings datasets, the lowest performance seen for recordings #5 is most likely due to a gap between the ECG electrode and skin caused by the bending and reflexing motion artifacts.

By using the sample-by-sample windowing process, the SegMA method can be utilized for both Heart Rate monitoring and HRV analysis in both frequency- and time-domains. From the Results section, it can be observed that the method is able to replicate both the low frequency (0.04-0.15 Hz) and the high frequency (0.15-0.4) dynamics well, albeit better the former than the latter, when compared to the reference HRV. For time-domain HRV measures, the mean HR, SDNN, RMSSD, and pNN50 from the SegMA method were all found to be not significantly different than the reference HRV. It has long been shown that during dynamic exercise, heart rate increases due to both parasympathetic withdrawal and an augmented sympathetic activity (Iellamo, F., Neural mechanisms of cardiovascular regulation during exercise. Auton Neurosci, 2001. 90 (1-2):p. 66-75; Bernardi, L. and M. F. Piepoli, [Autonomic nervous system adaptation during physical exercise]. Ital Heart J Suppl, 2001. 2 (8): p. 831-9). The relative role of the two drives depends on the movement intensity (Sarmiento, S., et al., Heart rate variability during high-intensity exercise. Journal of Systems Science and Complexity, 2013. 26 (1): p. 104-116; Roure, R., et al., Autonomic nervous system responses correlate with mental rehearsal in volleyball training. Eur J Appl Physiol Occup Physiol, 1998. 78 (2): p. 99-108; Perini, R., et al., The influence of exercise intensity on the power spectrum of heart rate variability. Eur J Appl Physiol Occup Physiol, 1990. 61 (1-2): p. 143-8). Analysis of HRV permits insight into these control mechanisms (Aubert, A. E., B. Seps, and F. Beckers, Heart rate variability in athletes. Sports Med, 2003. 33 (12): p. 889-919). HRV analysis from ECG during severe movements and physical activities has been problematic in the past. With SegMA, missing portions of corrupted data during severe motion artifacts can reconstructed with a good confidence.

The SegMA method can be implemented in real time. The method written in Matlab® takes around 75 msec on data segmented into 8 seconds. Therefore, given the high accuracy of SegMA in estimating HR despite severe motion artifacts, SegMA has the potential to be applicable for real-time implementation on wearable devices such as smart watches and ECG-based fitness sensors.

Figure 15:
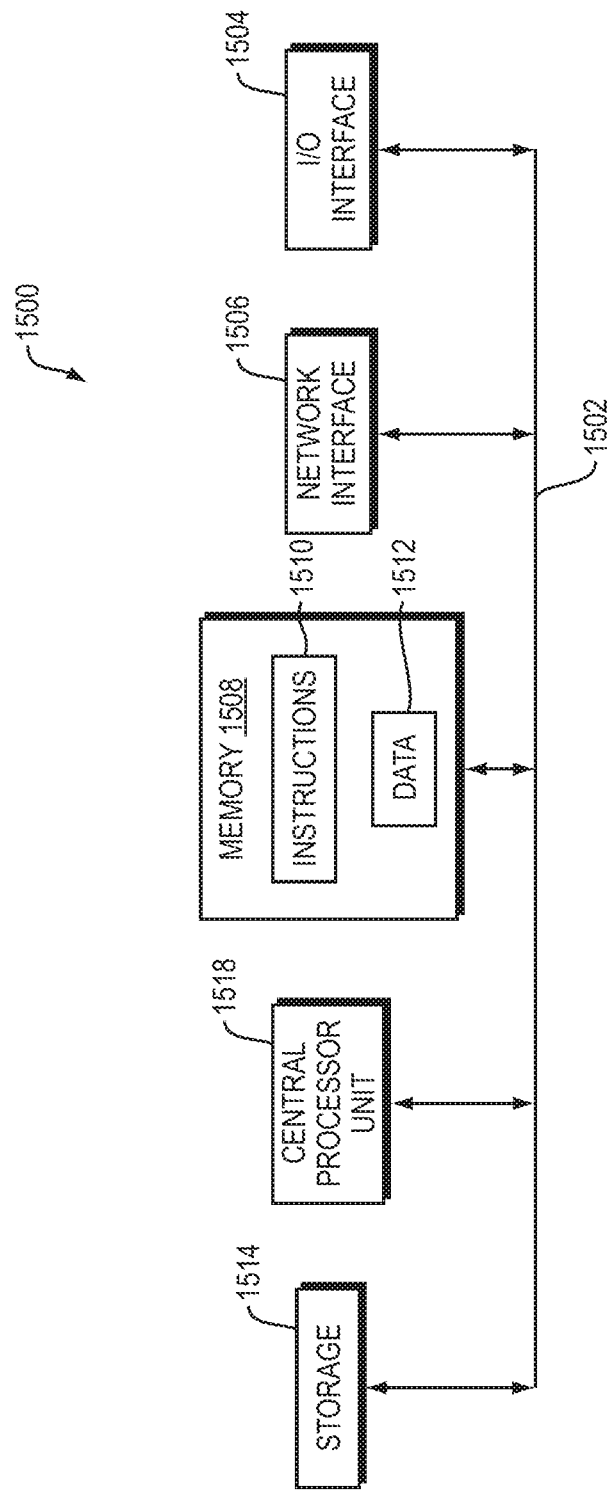
FIG. 15 is a block diagram of an example internal structure of a computer optionally within an embodiment disclosed herein.

FIG. 15 is a block diagram of an example of the internal structure of a computer 1500 in which various embodiments of the present disclosure may be implemented. The computer 1500 contains a system bus 1502, where a bus is a set of hardware lines used for data transfer among the components of a computer or processing system. The system bus 1502 is essentially a shared conduit that connects different elements of a computer system (e.g., processor, disk storage, memory, input/output ports, network ports, etc.) that enables the transfer of information between the elements. Coupled to the system bus 1502 is an I/O device interface 1504 for connecting various input and output devices (e.g., keyboard, mouse, displays, printers, speakers, etc.) to the computer 1500. A network interface 1506 allows the computer 1500 to connect to various other devices attached to a network. Memory 1508 provides volatile storage for computer software instructions 1510 and data 1512 that may be used to implement embodiments of the present disclosure. Disk storage 1514 provides non-volatile storage for computer software instructions 1510 and data 1512 that may be used to implement embodiments of the present disclosure. A central processor unit 1518 is also coupled to the system bus 1502 and provides for the execution of computer instructions.

Further example embodiments disclosed herein may be configured using a computer program product; for example, controls may be programmed in software for implementing example embodiments. Further example embodiments may include a non-transitory computer-readable medium containing instructions that may be executed by a processor, and, when loaded and executed, cause the processor to complete methods described herein. It should be understood that elements of the block and flow diagrams, such as the reconstruction unit 416, output unit 418, pre-processing unit 515, reconstruction unit 516, output unit 518, heart rate unit, arterial oxygen saturation (SpO2) unit, and ailment unit, disclosed above, may be implemented in software, hardware, such as via one or more arrangements of circuitry of FIG. 15, disclosed above, or equivalents thereof, firmware, a combination thereof, or other similar implementation determined in the future. In addition, the elements of the block and flow diagrams described herein may be combined or divided in any manner in software, hardware, or firmware. If implemented in software, the software may be written in any language that can support the example embodiments disclosed herein. The software may be stored in any form of computer readable medium, such as random access memory (RAM), read only memory (ROM), compact disk read-only memory (CD-ROM), and so forth. In operation, a general purpose or application-specific processor or processing core loads and executes software in a manner well understood in the art. It should be understood further that the block and flow diagrams may include more or fewer elements, be arranged or oriented differently, or be represented differently. It should be understood that implementation may dictate the block, flow, and/or network diagrams and the number of block and flow diagrams illustrating the execution of embodiments disclosed herein.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for reconstructing a heart-related signal output by a biomedical sensor, the method comprising:
pre-processing the heart-related signal to produce a pre-processed heart-related signal;
reconstructing a representation of the heart-related signal to produce a reconstructed representation of the heart-related signal, the reconstructing based on a time-varying spectral analysis of the pre-processed heart-related signal, the heart-related signal including motion artifacts, the motion artifacts being signal artifacts produced by movement of the biomedical sensor relative to a sensing location, the pre-processing reducing the motion artifacts in the pre-processed heart-related signal for the reconstructing, the heart-related signal being an electrocardiogram (ECG) signal; and
outputting the reconstructed representation of the heart-related signal.

2. The method of claim 1, wherein the biomedical sensor is an electrocardiogram (ECG) sensor.

3. The method of claim 1, wherein the reconstructing further reduces the motion artifacts reduced by the pre-processing.

4. The method of claim 1, wherein the pre-processing includes down-sampling the heart-related signal to produce a down-sampled heart-related signal, the down-sampling being at a sampling rate less than an original sampling rate.

5. The method of claim 4, wherein:
the time-varying spectral analysis is based on a frequency resolution; and
the down-sampling affects the frequency resolution of the time-varying spectral analysis.

6. The method of claim 4, wherein the pre-processing includes computing a derivative of the down-sampled heart-related signal to reduce the motion artifacts.

7. The method of claim 6, wherein the pre-processing further includes computing an absolute value of the derivative to further reduce the motion artifacts.

8. The method of claim 1, wherein the time-varying spectral analysis includes computing a time-frequency spectrum (TFS) of the pre-processed heart-related signal.

9. The method of claim 8, wherein the TFS computed is a 3-dimensional spectra including a time-varying amplitude or power distribution with respect to time and frequency.

10. The method of claim 8, wherein the TFS computed is a time-varying power spectral density (PSD).

11. The method of claim 8, further including limiting the TFS computed to a given frequency range.

12. The method of claim 11, wherein the given frequency range is 0.5 Hz to 3 Hz.

13. The method of claim 8, wherein:
the TFS is computed for each shift of a windowed data segment of the pre-processed heart-related signal; and
the heart related signal is reconstructed for each shift of the windowed data segment.

14. The method of claim 13, wherein, at each shift of the windowed data segment subsequent to an initial windowed data segment, the method further includes:
retaining up to a pre-determined number of frequency spectra to produce a subset of frequency spectra; and
selecting a frequency component to produce a selected frequency component for the reconstructing, the selected frequency component selected from amongst frequency components of the subset of frequency spectra and a previous frequency component, the previous frequency component having been selected for a previous shift of the windowed data segment to reconstruct the heart-related signal for the previous shift.

15. The method of claim 1, wherein the time-varying spectral analysis is a first time-varying spectral analysis and wherein the reconstructing is further based on a second time-varying spectral analysis of a motion signal, the motion signal output by a motion sensor and representative of the motion artifacts in the heart-related signal.

16. The method of claim 15, further including employing the second time-varying spectral analysis of the motion signal to produce a movement classification of the movement, and wherein the reconstructing is further based on the classification of the movement.

17. The method of claim 15, wherein the heart-related signal and the motion signal are output, concurrently.

18. The method of claim 15, wherein the biomedical sensor and the motion sensor are co-located.

19. The method of claim 15, wherein the motion sensor is an accelerometer.

20. The method of claim 1, further comprising employing the reconstructed representation to determine a heart rate estimate.

21. The method of claim 1, further comprising employing the reconstructed representation to determine a heart rate variability (HRV) estimate.

22. The method of claim 1, further comprising employing the reconstructed representation to detect or predict a heart-related ailment, the heart-related ailment including at least one of a heart rate variability (HRV) condition, atrial fibrillation condition, congestive heart failure condition, and tachycardia condition.

23. The method of claim 1, wherein the pre-processing, the reconstructing, and the outputting are performed in real-time with respect to outputting of the heart-related signal by the biomedical sensor.

24. The method of claim 1, wherein the pre-processing, the reconstructing, and the outputting are performed in non-real-time with respect to outputting of the heart-related signal by the biomedical sensor.

25. An apparatus for reconstructing a heart-related signal output by a biomedical sensor, the apparatus comprising:
a pre-processing unit configured to pre-process the heart-related signal to produce a pre-processed heart-related signal;
a reconstruction unit configured to reconstruct a representation of the heart-related signal to produce a reconstructed representation of the heart-related signal, the reconstructing based on a time-varying spectral analysis of the pre-processed heart-related signal, the heart-related signal including motion artifacts, the motion artifacts being signal artifacts produced by movement of the biomedical sensor relative to a sensing location, the pre-processing unit reducing the motion artifacts in the pre-processed heart-related signal for the reconstructing, the heart-related signal being an electrocardiogram (ECG) signal; and
an output unit configured to output the reconstructed representation of the heart-related signal.

26. The apparatus of claim 25, wherein the biomedical sensor is an electrocardiogram (ECG) sensor.

27. The apparatus of claim 25, wherein the reconstruction unit further reduces the motion artifacts reduced by the pre-processing unit.

28. The apparatus of claim 25, wherein pre-processing by the pre-processing unit includes down-sampling the heart-related signal to produce a down-sampled heart-related signal, the down-sampling being at a sampling rate less than an original sampling rate.

29. The apparatus of claim 28 wherein:
the time-varying spectral analysis is based on a frequency resolution; and
the down-sampling affects the frequency resolution of the time-varying spectral analysis.

30. The apparatus of claim 28, wherein the pre-processing unit is further configured to compute a derivative of the down-sampled heart-related signal to reduce the motion artifacts.

31. The apparatus of claim 30, wherein the pre-processing unit is further configured to compute an absolute value of the derivative to further reduce the motion artifacts.

32. The apparatus of claim 25, wherein the reconstruction unit is further configured to perform the time-varying spectral analysis by computing a time-frequency spectrum (TFS) of the pre-processed heart-related signal.

33. The apparatus of claim 32, wherein the TFS computed is a 3-dimensional spectra including a time-varying amplitude or power distribution with respect to time and frequency.

34. The apparatus of claim 32, wherein the TFS computed is a time-varying power spectral density (PSD).

35. The apparatus of claim 32, wherein the reconstruction unit is further configured to limit the TFS computed to a given frequency range.

36. The apparatus of claim 35, wherein the given frequency range is 0.5 Hz to 3 Hz.

37. The apparatus of claim 32, wherein:
the TFS is computed for each shift of a windowed data segment of the pre-processed heart-related signal; and
the reconstruction unit is further configured to reconstruct the heart related signal for each shift of the windowed data segment.

38. The apparatus of claim 37, wherein, at each shift of the windowed data segment subsequent to an initial windowed data segment, the reconstruction unit reconstructs the representation by:
retaining up to a pre-determined number of frequency spectra to produce a subset of frequency spectra; and
selecting a frequency component to produce a selected frequency component for the reconstructing, the selected frequency component selected from amongst frequency components of the subset of frequency spectra and a previous frequency component, the previous frequency component having been selected for a previous shift of the windowed data segment to reconstruct the heart-related signal for the previous shift.

39. The apparatus of claim 25, wherein the time-varying spectral analysis is a first time-varying spectral analysis and wherein the reconstruction unit is further configured to perform the reconstructing based on a second time-varying spectral analysis of a motion signal, the motion signal output by a motion sensor and representative of the motion artifacts in the heart-related signal.

40. The apparatus of claim 39, wherein the reconstruction unit is further configured to employ the second time-varying spectral analysis of the motion signal to produce a movement classification of the movement, and wherein the reconstructing is further based on the classification of the movement.

41. The apparatus of claim 39, wherein the heart-related signal and the motion signal are output by the biomedical sensor and the motion sensor, respectively, concurrently.

42. The apparatus of claim 39, wherein the apparatus includes the biomedical sensor and the motion sensor.

43. The apparatus of claim 39, wherein the motion sensor is an accelerometer.

44. The apparatus of claim 25, further comprising a heart rate unit configured to employ the reconstructed representation to determine a heart rate estimate.

45. The apparatus of claim 25, further comprising a heart rate variability (HRV) unit configured to employ the reconstructed representation to determine a heart rate variability (HRV) estimate.

46. The apparatus of claim 25, further comprising an ailment unit configured to employ the reconstructed representation to detect or predict a heart-related ailment, the heart-related ailment including at least one of a heart rate variability (HRV) condition, atrial fibrillation condition, congestive heart failure condition, and tachycardia condition.

47. The apparatus of claim 25, wherein the reconstruction unit, the output unit, and the pre-processing unit are configured to reconstruct, pre-process, and output, respectively, in real-time with respect to outputting of the heart-related signal by the biomedical sensor.

48. The apparatus of claim 25, wherein the reconstruction unit, the output unit, and the pre-processing unit are configured to reconstruct, pre-process, and output, respectively, in non-real-time with respect to outputting of the heart-related signal by the biomedical sensor.

49. A non-transitory computer-readable medium having encoded thereon a sequence of instructions which, when loaded and executed by a processor, causes the processor to reconstruct a heart-related signal output by a biomedical sensor, the processor reconstructing the heart-related signal by:

pre-processing the heart-related signal to produce a pre-processed heart-related signal;

reconstructing a representation of the heart-related signal to produce a reconstructed representation of the heart-related signal, the reconstructing based on a time-varying spectral analysis of the pre-processed heart-related signal, the heart-related signal including motion artifacts, the motion artifacts being signal artifacts produced by movement of the biomedical sensor relative to a sensing location, the pre-processing reducing the motion artifacts in the pre-processed heart-related signal for the reconstructing, the heart-related signal being an electrocardiogram (ECG) signal; and outputting the reconstructed representation of the heart-related signal.

* * * * *